United States Patent
Diamond et al.

(10) Patent No.: US 6,630,478 B2
(45) Date of Patent: Oct. 7, 2003

(54) METHODS FOR TREATMENT OF DRUG-INDUCED PERIPHERAL NEUROPATHY

(75) Inventors: Jack Diamond, Hamilton (CA); Alvin J. Glasky, Tustin, CA (US); Mark M. Foreman, Tustin, CA (US)

(73) Assignee: NeoTherapeutics, Inc., Irvine, CA (US)

( * ) Notice: Subject to any disclaimer, the term of this patent is extended or adjusted under 35 U.S.C. 154(b) by 0 days.

(21) Appl. No.: 09/899,901

(22) Filed: Jul. 6, 2001

(65) Prior Publication Data

US 2002/0061899 A1 May 23, 2002

Related U.S. Application Data

(60) Provisional application No. 60/216,844, filed on Jul. 7, 2000.

(51) Int. Cl.$^7$ .............................................. A61K 31/52
(52) U.S. Cl. ........................................................ 514/262
(58) Field of Search ........................................ 514/262

(56) References Cited

U.S. PATENT DOCUMENTS

| | | | |
|---|---|---|---|
| 3,300,380 A | 1/1967 | Gray et al. | 167/65 |
| 3,321,369 A | 5/1967 | Glasky et al. | 167/65 |
| 3,438,968 A | 4/1969 | Glasky et al. | 260/211.5 |
| 3,666,856 A | 5/1972 | Elion et al. | 424/180 |
| 4,035,486 A | 7/1977 | Laborit | 424/178 |
| 4,138,562 A | 2/1979 | Vince | 544/326 |
| 4,221,794 A | 9/1980 | Simon et al. | 424/253 |
| 4,221,909 A | 9/1980 | Simon et al. | 544/265 |
| 4,221,910 A | 9/1980 | Giner-Sorolla | 544/265 |
| 4,315,920 A | 2/1982 | Schaeffer et al. | 424/180 |
| 4,340,726 A | 7/1982 | Simon et al. | 536/17.4 |
| 4,347,360 A | 8/1982 | Ogilvie | 544/276 |
| 4,451,478 A | 5/1984 | Simon et al. | 424/273 R |
| 4,643,992 A | 2/1987 | Goodman et al. | 514/45 |
| 4,952,693 A | 8/1990 | Sircar et al. | 544/255 |
| 5,023,244 A | 6/1991 | Goto et al. | 514/46 |
| 5,091,432 A | 2/1992 | Glasky | 514/262 |
| 5,093,318 A | 3/1992 | Goodman et al. | 514/45 |
| 5,187,162 A | 2/1993 | Marangos et al. | 514/46 |
| 5,237,051 A | 8/1993 | Garbers et al. | 530/350 |
| 5,256,677 A | 10/1993 | Sham et al. | 514/351 |
| 5,376,642 A | 12/1994 | Yarchoan et al. | 514/45 |
| 5,447,939 A | * 9/1995 | Glasky et al. | 514/310 |
| 5,565,437 A | 10/1996 | Marquez et al. | 514/45 |
| 5,595,901 A | 1/1997 | Rocancourt et al. | 435/232 |
| 5,795,756 A | 8/1998 | Johnson et al. | 435/183 |
| 5,801,159 A | 9/1998 | Miller et al. | 514/45 |
| 5,801,184 A | 9/1998 | Glasky et al. | 514/310 |
| 5,948,771 A | 9/1999 | Danziger | 514/185 |
| 6,027,936 A | 2/2000 | Glasky | 435/325 |

FOREIGN PATENT DOCUMENTS

| | | |
|---|---|---|
| WO | WO 99/56550 | 11/1999 |
| WO | WO 99/57119 | 11/1999 |
| WO | WO 99/57120 | 11/1999 |

OTHER PUBLICATIONS

Stedman's Medical Dictionary, pp. 243–244 (1995).*
N.W. Tietz, ed., "Textbook of Clinical Chemistry" (W.B. Saunders Co., Philadelphia, 1986), pp. 882–886.
G.A. Lyles & B. A. Callingham, "The Effects of Thyroid Hormones on Monoamine Oxidase in the Rat Heart," *J. Pharm. Pharmacol.* 26:921–930 (1974).
S.K. Gupta & R.K. Mishra, "Desensitization of $D_1$ Dopamine Receptors Down–Regulates the $G_s\alpha$ Subunit of G Protein in SK–N–MC Neuroblastoma Cells," *J. Mol. Neurosci.* 4: 117–123 (1993).
S.K. Gupta & R.K. Mishra, "Up–Regulation of $D_1$ Dopamine Receptors in SK–N–MC Cells After Chronic Treatment with SCH 23390," *Neurosci. Res. Commun.* 15: 157–166 (1994).
P.W. Baures et al., "Design, Synthesis, X–Ray Analysis, and Dopamine Receptor–Modulating Activity of Mimics of the C5' Hydrogen–Bonded Conformation in the Peptidomimetic 2–Oxo–3–(R)–[(2(S)–Pyrrolidinylcarbonyl)amino]–1–Pyrrolidineacetamide," *J. Med. Chem.* 37: 3677–3683 (1994).
J.E. Savelli et al., "Modulation of N–Methyl–D–Aspartate (NMDA) Antagonist–Induced Darting Behaviour by the Peptidomimetic PAMTA,", *Brain Res.* 682: 41–49 (1995).
K.A. Jacobson, "Chemical Approaches to the Definition of Adenosine Receptors" *In Adenosine Receptors* (D.M.F. Cooper & C. Londos, eds., *Receptor Biochemistry and Methodology*, J.C. Venter, L.C. Harrison, eds., Alan R. Liss: New York, 1988), pp. 11:1–26.
S.H. Appel & J.L. McManaman, "Is a Breakdown of the Blood–Brain Barrier Cause of Effect?," *Neurobiol. Aging* 7:512–514 (1986).
S.M. MacDonald et al., "Immunological Parametes in the Aged and in Alzheimer's Disease," *Clin. Exp. Immunol.* 49:123–128 (1982).
A.E. Miller et al., "Immunological Studies in Senile Dementia of the Alzheimer Type: Evidence for Enhanced Suppressor Cell Activity," *Ann. Neurol.* 10:506–510 (1981).
K. Stefansson, "Neuroimmunology of Aging" in *Clinical Neurology of Aging* (M.L. Albert, ed., Oxford University Press, Oxford, (1984)), ch. 4, pp. 76–94.

(List continued on next page.)

*Primary Examiner*—Phyllis G. Spivack
(74) *Attorney, Agent, or Firm*—Louis C. Cullman

(57) ABSTRACT

A method of treating drug-induced peripheral neuropathy comprising administering to a patient with drug-induced peripheral neuropathy an effective quantity of N-4-carboxaphenyl-3-(6-oxohydropurin-9-yl)propananide AIT-082, is disclosed. Peripheral nerve sprouting can be induced through the action of a neurotrophic factor such as nerve growth factor (NGF) without the occurrence of hyperalgesia. The peripheral nerve sprouting can be nociceptive nerve sprouting. The drug-induced peripheral neuropathy is associated with the administration of oncolytic drugs, such as a vinca alkaloid, cisplatin, paclitaxel, suramin, altretamine, carboplatin, chlorambucil, cytarabine, dacarbazine, docetaxel, etoposide, fludarabine, ifosfamide with mesna, tamoxifen, teniposide, or thioguanine.

9 Claims, 5 Drawing Sheets

OTHER PUBLICATIONS

L.R. Weitkamp et al., "Alzheimer Disease: Evidence for Susceptibility Loci on Chromosomes 6 and 14," *Am. J. Hum. Genet.* 35:443–53 (1983).

A. Yamazaki et al., Synthesis of Guanosine and Its Derivatives from 5–Amino–1–β–D–Ribofuranosyl–4–Imidazolecarboxamide I. Ring Closure with Benzoyl Isothiocyanate, *J. Org. Chem.* 32:1825–1828 (1967).

B. Alhede et al., "A Simple and Efficient Synthesis of 9–Substituted Guanines. Cyclodesulfurization of 1–Substituted 5–[(Thiocarbamoyl)amino]imidazole–4–carboxamides under Aqueous Basic Conditions," *J. Org. Chem.* 56:2139–2143 (1991).

R.E. Callard & A.J.H. Gearing, "The Cytokine Facts Book" (Academic Press, London, 1994), pp. 99–100, 104–105, 191–200, 235–237.

P.J. Middlemiss et al., "AIT–082, a Unique Purine Derivative, Enhances Nerve Growth Factor Mediated Neurite Outgrowth from PC12 Cells," *Neurosci. Lett.* 199: 131–134 (1995).

K.L. Audus et al., "Brain Uptake of Drugs: the Influence of Chemical and Biological Factors," *Adv. Drug Res.* 23: 1–64 (1992).

W.A. Banks & A.J. Kastin, "Measurement of Transport of Cytokines Across the Blood–Brain Barrier," *Meth. Neurosci.* 16: 67–77 (1993).

A.L. Betz, "Identification of Hypoxanthine Transport and Xanthine Oxidase Activity in Brain Capillaries," *J. Neurochem.* 44:574–579 (1985).

K.G. Blasberg et al., "Transport of α–Aminoisobutyric Acid Across Brain Capillary and Cellular Membranes," *J. Cereb. Blood Flow Metab.* 3: 8–32 (1983).

E.M. Cornford & W.H. Olendorf, "Independent Blood–Brain Barrier Transport Systems for Nucleic Acid Precursors," *Biochim. Biophys. Acta* 394: 211–219 (1975).

A.J. Glasky et al., "Effect of AIT–082, a Purine Analog, on Working Memory in Normal and Aged Mice," *Pharmacol. Biochem. Behav.* 47: 325–329 (1994).

A.J. Glasky et al., "Neurotrophins, Growth Factors and Mimetic Agents as Neuroprotectors in the Treatment of Alzheimer's Disease" *In Alzheimer Disease: From Molecular Biology to Therapy* (R. Becker & E. Giacobini, eds., Birkhäuser, Boston, 1996), pp. 119–124.

E.G. Gutierrez et al., "Murine Tumor Necrosis Factor Alpha Is Transported from Blood to Brain in the Mouse," *J. Neuroimmunol.* 47: 169–176 (1993).

M. Hosokawa & M. Ueno, "Aging of Blood–Brain Barrier and Neuronal Cells of Eye and Ear in SAM Mice," *Neurobiol. Aging* 20:117–123 (1999).

M.D. Johnson & B.D. Anderson, "Localization of Purine Metabolizing Enzymes in Bovine Brain Microvessel Endothelial Cells: An Enzymatic Blood–Brain Barrier for Dideoxynucleosides?," *Pharm. Res.* 13: 1881–1886 (1996).

A.D. Mooradian, "Effect of Aging on the Blood–Brain Barrier," *Neurobiol. Aging* 9: 31–39 (1988).

W. Pan et al., "Permeability of the Blood–Brain Barrier to Neurotrophins," *Brain Res.* 788:87–94 (1998).

W.M. Pardridge, "CNS Drug Design Based on Principles of Blood–Brain Barrier Transport," *J. Neurochem.* 70: 1781–1792 (1988).

J.F. Poduslo et al., "Macromolecular Permeability Across the Blood–Nerve and Blood–Brain Barriers," *Proc. Natl. Acad. Sci USA* 91: 5705–5709 (1994).

J.F. Poduslo & G.L. Curran, "Permeability at the Blood–Brain Barrier and Blood–Nerve Barriers of the Neurotrophic Factors: NGF, CNTF, NT–3, BDNF," *Mol. Brain Res.* 36: 280–286 (1996).

J.J. Ramirez et al., "AIT–082 Accelerates Septodentate Sprouting After Unilateral Entorhinal Cortex Lesion in Rats," *Soc. Neurosci. Abstr.* 24: 1942 (1998).

G.N. Shah & A.D. Mooradian, "Age–Related Changes in the Blood–Brain Barrier," *Exp. Gerontol.* 32: 501–519 (1997).

I. Skogg et al., "A Population Study on Blood–Brain Barrier Function in 85–Year–Olds: Relation to Alzheimer's Disease and Vascular Dementia," *Neurology* 50:966–917 (1998).

R. Spector, "Hypoxanthine Transport Through the Blood–Brain Barrier," *Neurochem. Res.* 12: 791–796 (1987).

R. Spector, "Hypoxanthine Transport and Metabolism in the Central Nervous System," *J. Neurochem.* 50:969–978 (1988).

D. Triguero et al., "Capillary Depletion Method for Quantitation of Blood–Brain Transport of Circulating Peptides and Plasma Proteins," *J. Neurochem.* 54: 1882–1888 (1990).

W.A. Banks et al., "Measurement of Efflux Rates from Brain to Blood" in *Methods in Molecular Biology, Neuropeptide Protocols* (G.B. Irvine & C.H. Williams, eds., Humana Press, Totowa, NJ, 1977), pp. 353–360.

M.P. Rathbone et al., "Physiology and Pharmacology of Natural and Synthetic Nonadenine–Based Purines in the Nervous System," *Drug Develop. Res.* 45: 356–372 (1998).

M.P. Rathbone et al., AIT–082 as a Potential Neuroprotective and Regenerative Agent in Stroke and Central Nervous System Injury, *Exp. Opin. Invest. Drugs* 8: 1255–1262 (1999).

W.A. Banks et al., "Effects of Wheatgerm Agglutinin and Aging on the Regional Brain Uptake of HIV–1 gp120," *Life Sci.* 65: 81–89 (1999).

J.S. Bintner et al., "AIT–082, a Hypoxanthine Derivative, Prevents Much of the Decrease in Cerebellar Neuron ATP Following Glutamate Exposure," *Soc. Neurosci.* 25: 2131 (1999) (abstract).

R. Huang et al., "Enhancement of Neuronal Cell Excitability by AIT–082 in Rat Hippocampal Neurons and Its Effects on Second Messenger Systems," *Soc. Neurosci.* 24: 1941 (1988) (abstract).

O. Chu–LaGraff et al., "Effect of AIT–082 on Brain NGF mRNA Levels and Transport of AIT–082 Across the Blood–Brain Barrier," *Soc. Neurosci.* 24: 1941 (1998) (abstract).

F. Caciagli et al., "The Hypoxanthine Derivative AIT–082 Protects Against Neurotoxicity in Vitro and in Vivo," *Soc. Neurosci.* 24: 1941 (1998) (abstract).

B.J.J. Juurlink et al., "The Hypoxanthine Analogue AIT–082 Promotes Neurite Formation and Regeneration in Cultured Hippocampal Neurons," *Soc. Neurosci* 24: 1941 (1998) (abstract).

E.M. Taylor et al., "$^{14}$C–AIT082 Crosses the Blood–Brain Barrier and Is Pumped Out of Brain by a Probenecid– and Verapamil–Sensitive Mechanism," *Soc. Neurosci.* 25: 1758 (1999) (abstract).

F. Caciagli et al., "The Hypoxanthine Analogue AIT–082 Mimics the Activity of Guanosine in Affecting Extracellular Adenosine Breakdown and Glutamate Reuptake in Rat Cultured Astrocytes," *Soc. Neurosci.* 25: 1195 (1999) (abstract).

R. Ciccarelli et al., "Guanosine and Related Drugs Stimulate the Production of Neurotrophic Factors from Rat Cultured Astrocytes by Involving Mitogen–Activated Protein Kinase Pathway," *Soc. Neurosci.* 25: 1013 (1999) (abstract).

P.J. Middlemiss et al., "The Synthetic Purine AIT–082 Enhances Recovery After Acute Spinal Cord Crush Injury in Rats," *Soc. Neurosci.* 25: 1002 (1999) (abstract).

P. Di Iorio et al., "The Hypoxanthine Derivative AIT–082 Is Protective Against NMDA– or Kainic Acid–Induced Rat Hippocampal Neurotoxicity in Vivo," *Soc. Neurosci.* 25: 756 (1999) (abstract).

A.G. Gittis & J.R. Puzuasky, "AIT–082 Improves Memory Performance in a Non–Match–to–Sample Task in Rats," *Soc. Neurosci.* 25: 62 (1999) (abstract).

G. Shaw et al., "Purines Pyrimidines, and Glyoxalines. Part XIII. Some New Unambiguous Syntheses of 5–Aminoglyoxalines and 5–Aminoglyoxaline–4–carboxamides, and a Synthesis of 5–Amino–1–β–D–ribofuranosylglyoxlaine–4–carboxyamide," *J. Chem. Soc. 1959:* 1648–(1959).

P.R. Birkett et al., "Synthesis and Intramolecular Cyclisation of 5–Aminoimidazolealkanoates and Their Conversion to Purine Derivatives," *Synthesis* 1991: 157–159 (1991).

G.M. Blackburn & M.J. Gait, eds., *Nucleic Acids in Chemistry and Biology* (2d ed., Oxford University Press, 1996), pp. 148–152.

S. Lehmann et al., "Neurite Outgrowth of Neurons of Rat Dorsal Root Ganglia Induced by New Neurotrophic Substances with Guanidine Group," *Neurosci. Lett.* 152:57–60 (1993).

M. Barinaga, "Carbon Monoxide: Killer to Brain Messenger in One Step," *Science* 259:309 (1993).

A. Verma et al., "Carbon Monoxide: A Putative Neural Messenger," *Science,* 259:381–384 (1993).

M. Zuo et al., "Nitric Oxide and Carbon Monoxide Produce Activity–Dependent Long–Term Synaptic Enhancement in Hippocampus," *Science* 260: 1946–1950 (1993).

ÅSeiger et al., "Intracranial Infusion of Purified Nerve Growth Factor to an Alzheimer Patient: The First Attempt of a Possible Future Treatment Strategy," *Behavioural Brain Res.* 57: 255–261 (1993).

A. Nitta et al., "Effects of Oral Administration of a Stimulator for Nerve Growth Factor Synthesis in Basal Forebrain–Lesioned Rats," *Eur. J. Pharmacol.* 250: 23–30 (1993).

M.H. Tuszynski & F.H. Gage, "Neurotrophic Factors and Neuronal Loss," In *Alzheimer Disease* (R.D. Terry et al., eds., Raven Press, New York, 1994), ch. 25, pp. 405–417.

R.D. Hawkins et al., "Nitric Oxide and Carbon Monoxide as Possible Retrograde Messengers in Hippocampal Long–Term Potentiation," *J. Neurobiol.* 25:652–665 (1994).

S.H. Snyder, "NO and CO: The Body's Unprecendented Signaling Molecules," *1995 Yearbook of Science and The Future, Engyclopedia Britannica,* pp. 84–101.

J.Z. Fields et al., "Cardiac Muscarinic Cholinergic Receptors: Biochemical Identification and Characterization," *I. Biol. Chem.* 253:3251–3258 (1978).

D.H. Maurice & R.J. Haslam, "Molecular Basis of The Synergistic Inhibition of Platelet Function by Nitrovasodilators and Activators of Adenylate Cyclase: Inhibition of Cyclic AMP Breakdown by Cyclic GMP," *Mol. Pharmacol.* 37:671–681 (1990).

I.D. Laviada et al., :Phosphatidylcholine–Phospholipase C Mediates the Induction of Nerve Growth Factor in Cultured Glial Cells, *FEBS Lett.* 364: 301–304 (1995).

A. Aurell et al., "The S–100 Protein in Cerebrospinal Fluid: A Simple ELISA Method," *J.Neurol. Sci.* 89: 157–164 (1989).

J. Barnett et al., "Human β Nerve Growth Factor Obtained from a Baculovirus Expression System Has Potent in Vitro and in Vivo Neurotrophic Activity," *Exp. Neurol.* 110:11–24 (1990).

M.M. Bradford, "A Rapid and Sensitive Method for the Quantitation of Microgram Quantities of Protein Using the Principle of Protein–Dye Binding," *Anal. Biochem.* 72:248–254 (1976).

A. Dhainaut et al., "New Purines and Purine Analogs as Modulators of Multi–Drug Resistance," *J. Med. Chem.* 39:4099–4108 (1996).

U. Diederichsen & H.W. Schmidt, "β–Homoalanyl–PNA: A Special Case of β–Peptides with β–Sheet–Like Backbone Conformation; Organization in Higher Ordered Structures," *Eur. J. Org. Chem.* 1998: 827–835 (1998).

M. Iwakawa et al., "Synthetic Routes to Nucleoside Analogs of N–Substituted 1,3–Thiazolidines," *Can. J. Chem.* 56:326–335 (1978).

M.L. Peterson & R. Vince, "Synthesis and Biological Evaluation of 4–Purinylpyrrolidine Nucleosides," *J. Med. Chem.* 34:2787–2795 (1991).

D.A. Nugiel et al., "Facile Preparation of 2,6–Disubstituted Purines Using Solid Phase Chemistry," *J. Org. Chem.J. Org. Chem.* 62:201–203 (1997).

K.G. Estep et al., "Synthesis and Structure–Activity Relationships of 6–Heterocyclic–Substituted Purines as Inactivation Modifiers of Cardiac Sodium Channels," *J. Med. Chem.* 38:2582–2595 (1995).

R.E. Dolle & D. NcNair, 9–(Sulfoximinoalkyl) Guanine Nucleosides as Potential Antiherpetic Agents,: *Tetrahedron Lett.* 34:1 (133–136) (1993).

S. Van Calenbergh et al., "Synthesis and Structure–Activity Relationship of Analogs of 2'–Deoxy–2'–(3–Methoxybenzamido)adenosine, a Selective Inhibitor of Trypanosomal Glycosomal Glyceraldehyde–3–Phospate Dehydrogenase," *J. Med. Chem.* 38:3838–3849 (1995).

D.L. Temple, JrI, "Substituted 6,7–Dihydroimidaxzo[1,2–α] Purin–9 (4H)–ones," *J. Med. Chem.* 23:1188–1198 (1980).

Y. Mizuno et al., "Novel Protecting Group for the Synthesis of 7α–D–Pentofuranosylhypoxanthines," *J. Org. Chem.* 37:30–42 (1972).

P.K. Bridson & T.P. Wierich, "Cycle Homologues of Xanthines. I. Imadazo[4,5–e][1,4]Diazepine–5,8–Diones." *J. Heterocyclic Chem.* 25:1179–1182 (1988).

P. Jimonet et al., "Riluzole Series. Synthesis and in Vivo "Antiglutamate" Activity of 6–Substituted–2–benzothiazolamines and 3–Substituted 2–imino–benzothiazolines," *J. Med. Chem.* 42:2828–2843 (1999).

D. Manetti et al., "Design, Synthesis, and Preliminary Pharmacological Evaluation of 1,4–Diazabicyclo[4.3.0] nonan–9–ones as a New Class of Highly Potent Nootropic Drugs." *J. Med. Chem.* 43:1969–1974 (2000).

D. Manetti et al., "Molecular Simplification of 1,4–Diazabicyclo[4.3.0]nonan–9–ones Given Piperazine Derivatives That Maintain High Nootropic Activity," *J. Med. Chem.* 43:4499–4507 (2000).

R.C. Polomano & G.J. Bennett, "Chemotherapy–evoked Painful Peripheral Neuropathy," *Pain Med.* 2:81–4 (2001).

S. De Santis et al., "Patients Treated with Antitumor Drugs Displaying Neurological Deficits Are Characterized by a Low Circulating Level of Nerve Growth Factor," *Clin. Cancer Res.* 6:90–95 (2000).

K. Hayakawa et al., "NGF Prevention of Neurotoxicity Induced by Cisplatin, Vincristine and Taxol Depends on Toxicity of EAch Drug and NGF Treatment Schedule: In Vitro Study of Adult Rat Sympathetic Ganglion Explants," *Brain Res.* 794:313–319 (1998).

C.M. Haskel and L. Rosen, "Cancel Treatment" 5$^{th}$ Ed. W.B. Saunders, Philadelphia, 2001), ch. 10, pp. 104–214 "Antineoplastic Agents".

K.M. Albers et al., "Overexpression of Nerve Growth Factor in Epidermis of Transgenic Mice Causes Hypertrophy of the Peripheral Nervous System," *J. Neurosci.* 14:1422–1432 (1994).

R.B. Campenot, "NGF and the Local Control of Nerve Terminal Growth," *J. Neurobiol.* 25:599–611 (1994).

M. Dantes & M. McComas, "The Extent and Time Course of Motoneuron Involvement in Amyotrophic Lateral Sclerosis," *Muscle & Nerve* 14:416–421 (1991).

B.M. Davis et al., "Overexpression of Nerve Growth Factor in Skin Causes Preferential Increases Among Innervation to Specific Sensory Targets," *J. Comp. Neurol.* 387:489–506 (1997).

J. Diamond et al., "NGF–Regulated Plasticity in the Adult Nervous System," *Soc. Neurosci. Abstr.* 14:245.6 (1988).

J. Diamond et al., "Trophic Regulation of Nerve Sprouting." *Science* 193:371–377 (1976).

J. Diamond et al., "Sensory Nerves in Adult Rats Regenerate and Restore Sensory Function to the Skin Independently of Endogenous NGF," *J. Neurosci.* 12:1467–1476 (1992).

J. Diamond et al., "Evidence that Endogenous β Nerve Growth Factor is Responsible for the Collateral Sprouting, but not the Regeneration, of Nociceptive Axons in Adult Rats," *Proc. Natl. Acad. Sci. USA,* 84:6596–6600 (1987).

J. Diamond et al., "Endogenous NGF and Nerve Impulses Regulate the Collateral Sprouting of Sensory Axons in the Skin of the Adult Rat," *J. Neurosi.* 12:1454–1466 (1992).

R. Doucette & J. Diamond, "Normal and Precocious Sprouting of Heat Nociceptors in the Skin of Adult Rats," *J. Comp. Neurol.* 261: 592–603 (1987).

K.B. English et al., "Localization of Nerve Growth Factor (NGF) and Low–Affinity NGF Receptors in Touch Domes and Quantification of NGF mRNA in Keratinocytes of Adult Rats," *J. Comp. Neurol.* 344:470–480 (1994).

A. Gloster, & J. Diamond, "Sympathetic Nerves in Adult Rats Regenerate Normally and Restore Pilomotor Function During an Anti–NGF Treatment that Prevents Their Collateral Sprouting," *J. Comp. Neurol.* 326:363–374 (1992).

S. Imayama, "Scanning and Transmission Electron Microscope Study on the Terminal Blood Vessels of the Rat Skin," *J. Invest. Dermatol.* 76:151–157 (1981).

P.C. Jackson & J. Diamond, "Temporal and Spatial Constraints on the Collateral Sprouting of Low–Threshold Mechanosensory Nerves in the Skin of Rats," *J. Comp. Neurol.* 226:336–345 (1984).

L.A Karchewski, et al., "Anatomical Evidence Supporting the Potential for Modulation by Multiple Neurotrophins in the Majority of Adult Lumbar Sensory Newrons," *J. Comp. Neurol.* 413:327–341 (1999).

S. Korsching & H. Thoenen, "Nerve Growth Factor Supply for Sensory Neurons: Site of Origin and Competition with the Sympathetic Nervous System," *Neurosci. Lett.* 54:201–205 (1985).

R. Levi–Montalcini et al., "Nerve Growth Factor:From Neurotrophin to Neurokine," *TINS* 19:514–520 (1996).

G.R. Lewin et al., "Nerve Growth Factor–induced Hyberalgesia in the Neonatal and Adult Rat," *J. Neurosci.* 13:2136–2148 (1993).

G.R. Lewis et al., "Peripheral and Central Mechanisms of NGF–induced Hyperalgesia," *Eur. J. Neurosci.* 6: 1903–1912 (1994).

K.M. Mearwo et al., "Increased NGF mRNA Expression in Denervated Rat Skin," *NeuroReport* 4: 351–354 (1993).

R.A. Murphy et al., "Immunological Relationships of NGF, BDNF, and NT–3: Recognition and Functional Inhibition by Antibodies to NGF," *J. Neurosci.* 13:2853–2862 (1993).

S. Neumann et al., "Inflammatory Pain Hypersensitivity Mediated by Phenotypic Switch in Myelinated Primary Sensory Neurons," *Nature* 384:360–364 (1996).

B.J. Nixon et al., "Impulse Activity Evokes Precocious Sprouting of Nociceptive Nerves into Denervated Skin," *Somatosensory Res.* 2:97–126 (1984).

E. Pertens et al., "Intraspinal and Behavioral Consequences of NGF–Induced Nociceptive Sprouting and NGF–Induced Hyperalgesia Compared in Adult Rats," *J. Comp. Neurol.* 410:73–89 (1999).

M.S. Ramer et al., "Glial Overexpression of NGF Enhances Neuropathic Pain and Adrenergic Sprouting into DRG Following Chronic Sciatic Constriction in Mice," *Neurosci. Lett.* 251:53–56 (1998).

M.I. Romero et al., "Extensive Sprouting of Sensory Afferents and Hyperalgesia Induced by Conditional Expression of Nerve Growth Factor in the Adult Spinal Cord," *J. Neurosci.* 20:4435–4445 (2000).

C.L. Stucky et al., "Overexpression of Nerve Growth Factor in Skin Selectively Affects the Survival and Functional Properties of Nociceptors," *J. Neurosci.* 19:8509–8516 (1999(.

E. Theriault and J. Diamond, "Nociceptive Cutaneous Stimuli Evoke Localized Constructions in a Skeletal Muscle," *J. Neurophysiol.* 60:446–462 (1988).

J.G. Toma et al., "Spatial Regulation of Neuronal Gene Expression in Response to Nerve Growth Factor," *Dev. Biol.* 184:1–9 (1997).

G.M. Yasargil et al., "Axonal Domains Within Shared Touch Domes in the Rat: A Comparison of Their Fate During Conditions Favoring Collateral Sprouting and Following Axonal Regeneration," *J. Comp. Neurol.* 270:301–312 (1988).

A.J. Glasky et al., "AIT–082, A Novel Purine Derivative with Neuroregenerative Properties," *Exp. Opin. Invest. Drugs* 6:1413–1417 (1997).

K. Hayakawa et al., "Nerve Growth Factor Prevents Neurotoxid Effects of Cisplatin, Vincristine and Taxol, on Adult Rat Sympathetic Ganglion Explants in Vitro," *Life Sci.* 55:591–525 (1994).

* cited by examiner

METHODS FOR TREATMENT OF DRUG-INDUCED PERIPHERAL NEUROPATHY

CROSS-REFERENCES

This application claims priority from Provisional Application Ser. No. 60/216,844, filed Jul. 7, 2000 by Jack Diamond and Alvin J. Glasky, and entitled "Methods for Treatment of Peripheral Neuropathy and Related Conditions with Bifunctional Purine Analogues," which is incorporated herein in its entirety by this reference.

BACKGROUND OF THE INVENTION

This invention is directed to methods for treatment of drug-induced peripheral neuropathy and related conditions, particularly drug-induced peripheral neuropathy associated with the administration of oncolytic drugs.

Many oncolytic or antineoplastic drugs have been developed in recent years. Although such drugs have proven effective in many cases in the treatment of malignancies, they can have severe side effects. One of the most serious and clinically significant side effect is peripheral neuropathy. Many antineoplastic drugs can cause peripheral neuropathy. For some of the most effective drugs, neurotoxicity is dose-limiting. It can force the termination of otherwise successful therapy, or can preclude the repetition of successful therapy. Sensory abnormalities produced by the administration of antineoplastic drugs can range from mild paresthesiae or dysesthesiae to severe neuropathic pain. In some cases, sensory and motor symptoms resolve within days or weeks after the agents are discontinued. However, peripheral neuropathy can be a chronic painful and disabling condition. The mechanisms that produce peripheral neuropathy as a consequence of the administration of oncolytic drugs are largely unknown (R. C. Polomano & G. J. Bennett, "Chemotherapy-evoked Painful Peripheral Neuropathy," *Pain Med.* 2: 8–14 (2001); S. De Santis et al., "Patients Treated with Antitumor Drugs Displaying Neurological Deficits Are Characterized by a Low Circulating Level of Nerve Growth Factor," *Clin. Cancer Res.* 6: 90–95 (2000); K. Hayakawa et al., "NGF Prevention of Neurotoxicity Induced by Cisplatin, Vincristine and Taxol Depends on Toxicity of Each Drug and NGF Treatment Schedule: In Vitro Study of Adult Rat Sympathetic Ganglion Explants," *Brain Res.* 794: 313–319 (1998)).

Accordingly, there is a need for more efficient methods of combating drug-induced peripheral neuropathy, particularly peripheral neuropathy induced by the administration of oncolytic drugs. Preferably, such methods should not interfere with cancer treatment or block the activity of the oncolytic drugs. Such methods should also not induce other side effects and should be well tolerated by cancer patients. Preferably, such methods should also combat peripheral neuropathy for all oncolytic drugs and should not depend on specific interactions with each individual oncolytic drug. There is a particular need for methods that can stimulate nerve growth or regeneration, particularly without inducing hyperalgesia.

SUMMARY

One embodiment of the present invention is a method of treating drug-induced peripheral neuropathy comprising administering to a patient with drug-induced peripheral neuropathy an effective quantity of an effective quantity of a compound comprising: (1) a moiety A selected from the group consisting of a purine moiety, a purine analogue, a tetrahydroindolone moiety, a tetrahydroindolone analogue, a pyrimidine moiety, a pyrimidine analogue and aminocarboxaminoimidazoles; (2) a hydrocarbyl moiety L of 1 to 6 carbon atoms that is linked to the moiety A and that can be cyclic, with the hydrocarbyl moiety being optionally substituted with one or more substituents selected from the group consisting of lower alkyl, amino, hydroxy, lower alkoxy, lower alkylamino, lower alkylthio, and oxo; and (3) a moiety B that is linked to the moiety L though a carbonyl group wherein B is —OZ or N($Y_1$)—D, where Z is hydrogen, alkyl, aryl, heteroaryl, cycloalkyl, aralkyl, or heteroaralkyl; D is a moiety that promotes absorption of the compound; and $Y_1$ is hydrogen, alkyl, aryl, heteroaryl, aralkyl, heteroaralkyl, alkanoyl, aroyl, heteroaroyl, aralkanoyl, heteroaralkanoyl, alkylsulfonyl, arylsulfonyl, heteroarylsulfonyl, aralkylsulfonyl, heteroaralkylsulfonyl, alkoxycarbonyl, aryloxycarbonyl, heteroaryloxycarbonyl, aralkoxycarbonyl, heteroaralkoxycarbonyl, alkylaminocarbonyl, arylaminocarbonyl, heteroarylaminocarbonyl, aralkylaminocarbonyl, or heteroaralkylaminocarbonyl, in which the alkyl portions can be cyclic and can contain from 1 to 3 heteroatoms, which can be N, O, or S.

The purine moiety can be selected from the group consisting of hypoxanthine and guanine, as well as other purine moieties. A number of purine derivatives suitable for use in methods according to the present invention are disclosed. In addition to these purines, analogues of naturally occuring purines defined above, tetrahydroindolones, tetrahydroindolone analogues, pyrimidines, pyrimidine analogues and aminocarboxaminoimidazoles, which maintain the proposed pharmacophore between the 6, 5, 4, and 9 positions on the purine molecule, may be used as alternatives to purines. Preferably, the compound is capable of passing through the blood-brain barrier.

Typically, the administration of the compound induces peripheral nerve sprouting in the skin of the patient to whom the purine derivative is administered. The peripheral nerve sprouting can be nociceptive nerve sprouting. Typically, the nociceptive nerve sprouting is induced without the occurrence of hyperalgesia.

The drug-induced peripheral neuropathy can be induced by the administration of an oncolytic drug such as a vinca alkaloid, cisplatin, paclitaxel, suramin, altretamine, carboplatin, chlorambucil, cytarabine, dacarbazine, docetaxel, etoposide, fludarabine, ifosfamide with mesna, tamoxifen, teniposide, or thioguanine. Methods according to the present invention are particularly significant in treating drug-induced peripheral neuropathy arising from the administration of vincristine, paclitaxel, or cisplatin.

BRIEF DESCRIPTION OF THE DRAWINGS

The following invention will become better understood with reference to the specification, appended claims, and accompanying drawings, where:

DESCRIPTION

Figure 1:
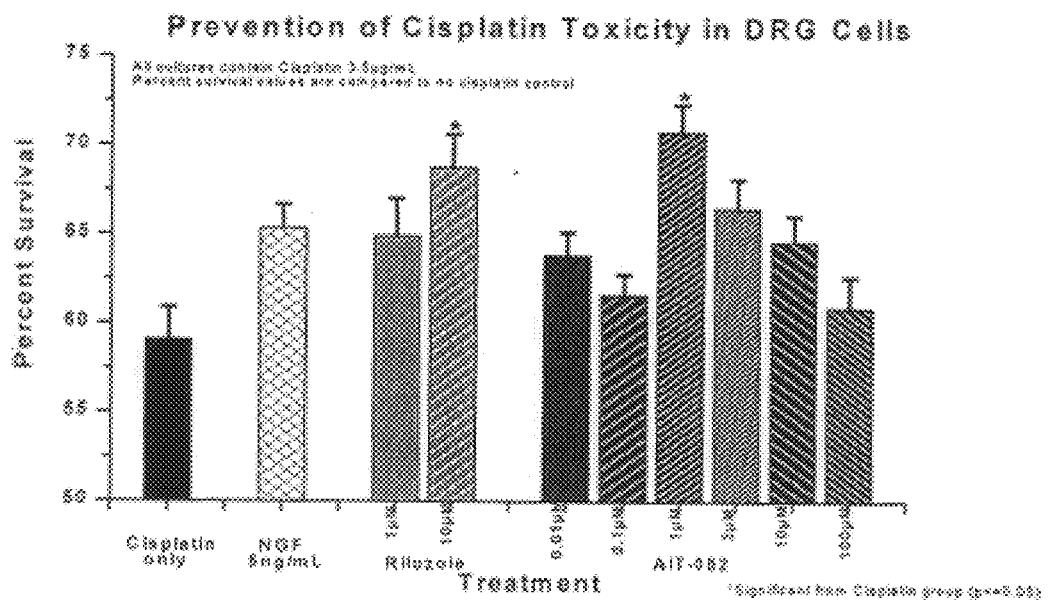
FIG. 1 is a bar graph showing the effects of riluzole and AIT-082 in the prevention of cisplatin toxicity in DRG cells.

We have discovered that the bifunctional purine derivative N-4-carboxyphenyl-3-(6-oxohydropurin-9-yl) propanamide (also known as AIT-082 and leteprinim potassium), which bypasses the blood-brain barrier, can act to induce peripheral nerve sprouting in the skin of adult rats. As detailed below in the Example, this activity may be attributable to upregulation of cutaneous nerve growth factor (NGF) levels induced by this bifunctional purine derivative, although Applicants do not intend to be bound by this theory. Moreover, this activity occurred without the induction of hyperalgesia. This property of acting to induce peripheral nerve sprouting, therefore, should also be possessed by other purine derivatives and analogues, tetrahydroindolone derivatives and analogues, and pyrimidine derivatives and analogues, as discussed below.

The peripheral nerve sprouting can be nociceptive nerve sprouting. The nociceptive nerve sprouting can occur without the induction of hyperalgesia.

Typically, a compound useful in a method of the present invention is capable of bypassing the blood-brain barrier.

More specifically, as detailed below in the Example, systematically administered AIT-082 closely mimics the effects both of increased levels of endogenous NGF, and of exogenous NGF. The compound induces vigorous collateral sprouting but has no effect on axonal regeneration after nerve crush (shown earlier to occur independently of NGF), and the sprouting it induced was blocked by systemic anti-NGF treatment. The growth of such nerve tissue is evoked and maintained entirely by the increased levels of NGF in adjacent denervated skin. However, AIT-082 resembles more the effects of increased endogenous NGF than of exogenous NGF, because it did not induce hyperalgesia. In fact, the sprouting evoked by AIT-082 was shown to be entirely attributable to the measured up-regulation it induced in endogenous NGF levels in skin.

Accordingly, one aspect of the present invention is a method of treating drug-induced peripheral neuropathy comprising administering to a patient with drug-induced peripheral neuropathy an effective quantity of a compound, the compound comprising: (1) a moiety A selected from the group consisting of a purine moiety, a purine analogue, a tetrahydroindolone moiety, a tetrahydroindolone analogue, a pyrimidine moiety, and a pyrimidine analogue; (2) a hydrocarbyl moiety L of 1 to 6 carbon atoms that is linked to the moiety A and that can be cyclic, with the hydrocarbyl moiety being optionally substituted with one or more substituents selected from the group consisting of lower alkyl, amino, hydroxy, lower alkoxy, lower alkylamino, lower alkylthio, and oxo; and (3) a moiety B that is linked to the moiety L though a carbonyl group wherein B is —OZ or N(Y$_1$)—D, where Z is hydrogen, alkyl, aryl, heteroaryl, cycloalkyl, aralkyl, or heteroaralkyl; D is a moiety that promotes absorption of the compound having activity against a multi-drug transporter protein; and Y$_1$ is hydrogen, alkyl, aryl, heteroaryl, aralkyl, heteroaralkyl, alkanoyl, aroyl, heteroaroyl, aralkanoyl, heteroaralkanoyl, alkylsulfonyl, arylsulfonyl, heteroarylsulfonyl, aralkylsulfonyl, heteroaralkylsulfonyl, alkoxycarbonyl, aryloxycarbonyl, heteroaryloxycarbonyl, aralkoxycarbonyl, heteroaralkoxycarbonyl, alkylaminocarbonyl, arylaminocarbonyl, heteroarylaminocarbonyl, aralkylaminocarbonyl, or heteroaralkylaminocarbonyl, in which the alkyl portions can be cyclic and can contain from 1 to 3 heteroatoms, which can be N, O, or S.

Typically, a compound useful in a method of the present invention is capable of passing through the blood-brain barrier.

In one preferred embodiment of methods according to the present invention, the moiety A is a purine moiety.

In one alternative, A is a substituted or unsubstituted hypoxanthine moiety. Typically, in this alternative, L has the structure —(CH$_2$)$_n$ where n is an integer from 1 to 6.

The compound having the activity against drug-induced peripheral neuropathy can be a compound of formula (I)

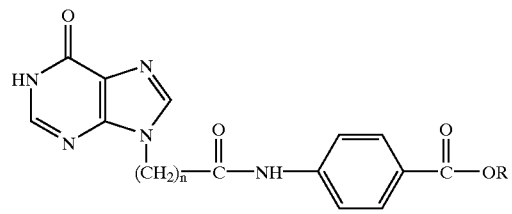

where n is an integer from 1 to 6 and R is hydrogen or lower alkyl or is a salt or prodrug ester of a compound of formula (I) wherein n is an integer from 1 to 6 and R is hydrogen or lower alkyl. Typically, the compound is a compound of formula (I) wherein n is an integer from 1 to 6 and R is hydrogen or lower alkyl. Typically, R is hydrogen, and the compound is N-4-[[3-(6-oxo-1,6-dihydropurin-9-yl)-1-oxopropyl]amino]benzoic acid, designated AIT-082. Alternatively, R is ethyl, and the compound is N-4-[[3-(6-oxo-1,6-dihydropurin-9-yl)-1-oxopropyl]amino]benzoic acid ethyl ester.

When the purine moiety is hypoxanthine, a preferred purine derivative is a compound of formula (I)

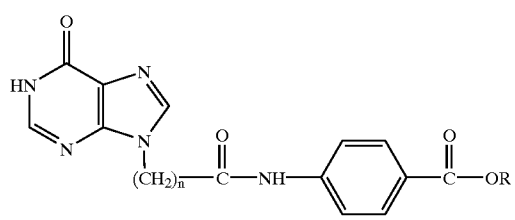

wherein n is an integer from 1 to 6 or of a salt or prodrug ester of formula (I) wherein n is an integer from 1 to 6. Typically, the purine derivative is a compound of formula (I) wherein n is an integer from 1 to 6. Preferably, n is 2 and the compound is N-4-carboxyphenyl-3-(6-oxohydropurin-9-yl) propanamide, also known as AIT-082. The activity of this compound is described further in the Example.

Alternatively, the purine derivative can be a 9-substituted hypoxanthine derivative of formula (II)

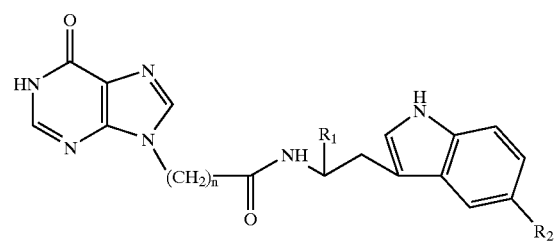

wherein n is a integer from 1 to 6, R$_1$ is selected from the group consisting of H, COOH, and COOW$_1$, where W$_1$ is selected from the group consisting of lower alkyl, amino, and lower alkylamino, and R$_2$ is selected from the group consisting of H and OH.

In this alternative, for one particularly preferred purine derivative, n is 2, $R_1$ is H and $R_2$ is OH and the purine derivative is N-(2-(5-hydroxyindol-3-yl))ethyl-3-(6-oxohydropurine-9-yl) propanamide. In this alternative, for another particularly preferred purine derivative, n is 2, $R_1$ is H and $R_2$ is H and the purine derivative is N-(2-indol-3-yl) ethyl-3-(6-oxohydropurin-9-yl) propanamide. In this alternative, for still another particularly preferred purine derivative, n is 2, $R_1$ is COOH, and $R_2$ is OH and the purine derivative is N-(1-carboxyl-(2-(5-hydroxyindol-3-yl))ethyl-3-(6-oxohydropurin-9-yl) propanamide.

As another alternative, the purine derivative can be a 9-substituted hypoxanthine derivative of formula (III)

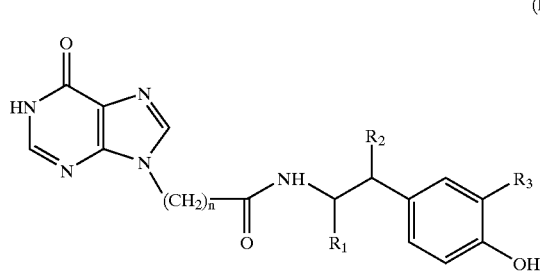

(III)

wherein n is an integer from 1 to 6, $R_1$ is selected from the group consisting of H, COOH, and $COOW_1$, wherein $W_1$ is selected from the group consisting of lower alkyl, amino, and lower alkylamino, $R_2$ is selected from the group consisting of H and OH, and $R_3$ is selected from the group consisting of H and OH.

In this alternative, for one particularly preferred purine derivative, n is 2, $R_1$ is H, $R_2$ is H, and $R_3$ is OH, and the purine derivative is N-(2-(3,4-dihydroxyphenyl))ethyl-3-(6-oxohydropurin-9-yl) propanamide. In this alternative, for another particularly preferred purine derivative, n is 2, $R_1$ is H, $R_2$ is OH, and $R_3$ is OH, and the purine derivative is N-(2-hydroxy-2-(3,4-dihydroxyphenyl))ethyl-3-(6-oxohydropurin-9-yl) propanamide. In this alternative, for still another particularly preferred purine derivative, n is 2, $R_1$ is COOH, $R_2$ is H, and $R_3$ is OH, and the purine derivative is N-(1-carboxyl-2-(3,4-dihydroxyphenyl))ethyl-3-(6-oxohydropurin-9-yl) propanamide.

When the purine moiety is guanine, one preferred purine derivative is a 9-substituted guanine derivative of formula (IV)

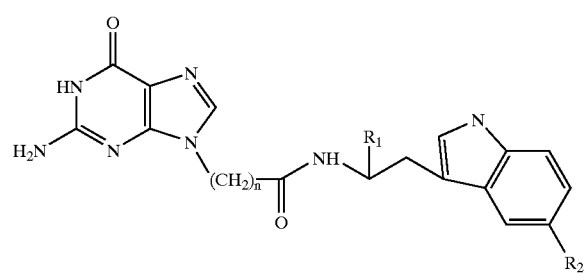

(IV)

wherein n is an integer from 1 to 6, $R_1$ is selected from the group consisting of H, COOH, and $COOW_1$, or $W_1$ is lower alkyl, amino, or lower alkylamino, and $R_2$ is selected from the group consisting of H and OH.

In this alternative, for one particularly preferred purine derivative, n is 2, $R_1$ is H, and $R_2$ is OH, and the purine derivative is N-(2-(5-hydroxindol-3-yl))ethyl-3-(2-amino-6-oxohydropurin-9-yl) propanamide. In this alternative, for another particularly preferred purine derivative, n is 2, $R_1$ is H, and $R_2$ is H and the purine derivative is N-(2-(2-indol-3-yl)ethyl))-3-(2-amino-6-oxohydropurin-9-yl)) propanamide. In this alternative, for still another particularly preferred purine derivative, n is 2, $R_1$ is COOH, and $R_2$ is OH, and the purine derivative is N-(1-carboxyl)-(2-(5-hydroxyindol-3-yl))ethyl-3-(2-amino-6-oxohydropurin-9-yl) propanamide.

Alternatively, the purine derivative can be a 9-substituted guanine derivative of formula (V) wherein n is an integer from 1 to 6.

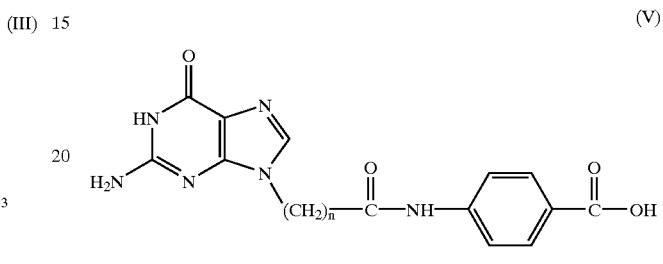

(V)

In this alternative, for one particularly preferred purine derivative, n is 2 and the compound is N-4-carboxyphenyl-3-(2-amino-6-oxohydropurin-9-yl) propanamide.

Alternatively, the purine derivative can be a 9-substituted guanine derivative of formula (VI) wherein n is an integer from 1 to 6.

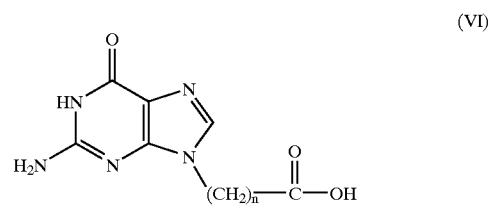

(VI)

In this alternative, for one particularly preferred purine derivative, n is 2 and the compound is 3-(2-amino-6-oxohydropurine-9-yl) propanoric acid.

Alternatively, the purine derivative can be a 9-substituted guanine derivative of formula (VII) wherein n is an in integer from 1 to 6, p is an integer from 1 to 6, and q is an integer from 1 to 3.

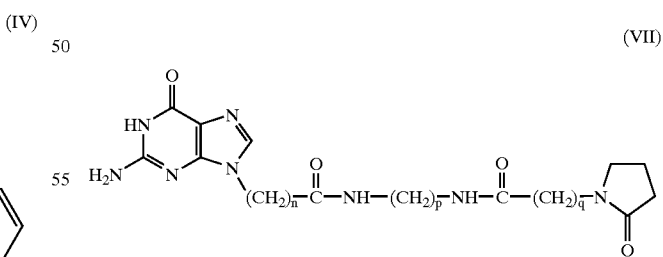

(VII)

In this alternative, for one particularly preferred purine derivative, n is 2, p is 2, and q is 1, and the purine derivative is N-[2-[[2-(2-oxopyrrolidin-1-yl)-1-oxoethyl]amino]ethyl] propanamide.

Alternatively, the purine derivative can be a 9-substituted guanine derivative of formula (VIII) wherein $R_1$ is selected from the group consisting of H, COOH, and $COOW_1$, where $W_1$ is selected from the group consisting of lower alkyl, amino, and lower alkylamino, $R_2$ is selected from the group consisting of H and OH, and $R_3$ is selected from the group consisting of H and OH.

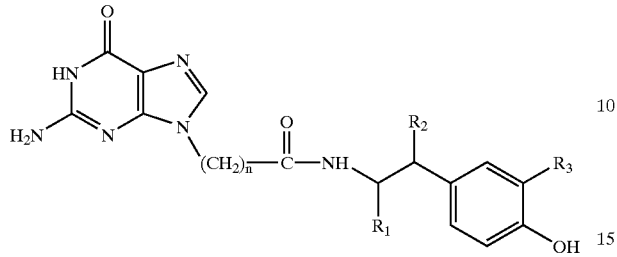

(VIII)

In this alternative, for one particularly preferred purine derivative, n is 2, $R_1$ is H, $R_2$ is H, and $R_3$ is OH, and the purine derivative is N-(2-(3,4-dihydroxyphenyl)ethyl-3-(2-amino-6-oxohydropurin-9-yl) propanamide. In this alternative, for another particularly preferred purine derivative, n is 2, $R_1$ is H, $R_2$ is OH, and $R_3$ is OH, and the purine derivative is N-(2-hydroxy-2-(3,4-dihydroxyphenyl) ethyl)-3-(2-amino-6-oxohydropurin-9-yl) propanamide. In this alternative, for still another particularly preferred purine derivative, n is 2, $R_1$ is COOH, $R_2$ is H, and $R_3$ is H and the compound is N-(1-carboxyl-2-(3,4-dihydroxyphenyl)ethyl)-3-(2-amino-6-oxohydropurin-9-yl) propanamide. Alternatively, the purine derivative can be a 9-substituted guanine derivative of formula (IX) wherein n is an integer from 1 to 6 and p is an integer from 1 to 3.

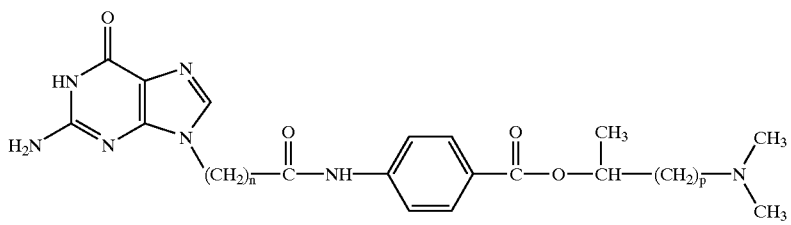

(IX)

In this alternative, for one particularly preferred purine derivative, n is 2, p is 1, and the compound is the 1-(dimethylamino)-2-propyl ester of N-4-carboxyphenyl-3-(2-amino-6-oxohydropurin-9-yl) propanamide.

Other bifunctional hypoxanthine derivatives suitable for use in methods according to the present invention are disclosed in U.S. Pat. No. 5,091,432 to Glasky, incorporated herein by this reference. Other bifunctional guanine derivatives suitable for use in methods according to the present invention are disclosed in U.S. patent application Ser. No. 09/49,153, by Glasky et al., incorporated herein by this reference.

More generally, purine-based compounds suitable for use in methods according to the present invention are compounds in which A is a substituted or unsubstituted 9-atom bicyclic moiety in which the 5-membered ring has 1 to 3 nitrogen atoms, the bicyclic moiety having the structure of formula (X)

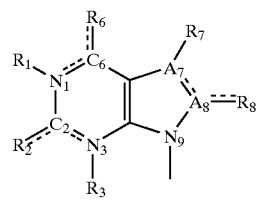

(X)

where:
(1) if the bond between $N_1$ and the bond between $C_5$ is a single bond, then the bond between $C_6$ and $R_6$ is a double bond, $R_6$ is O or S, and $R_1$ is hydrogen, alkyl, aralkyl, cycloalkyl, or heteroaralkyl;
(2) if the bond between $N_1$ and $C_6$ is a double bond, then the bond between $C_6$ and $R_6$ is a single bond, $R_1$ is not present, and $R_6$ is hydrogen, halo, amino, $OQ_1$, $SQ_1$, $NHNH_2$, $NHOQ_1$, $NQ_1Q_2$, or $NHQ_1$, where $Q_1$ and $Q_2$ are alkyl, aralkyl, heteroaralkyl, aryl, heteroaryl, alkanoyl, aroyl, aralkanoyl, heteroaralkanoyl, heteroaroyl, alkylsulfonyl, arylsulfonyl, heteroarylsulfonyl, aralkylsulfonyl, or heteroaralkylsulfonyl in which the alkyl portions can be cyclic and can contain from 1 to 3 heteroatoms which can be N, O, or S, and when $Q_1$, and $Q_2$ are present together and are alkyl, they can be taken together to form a 5- or 6-membered ring which can contain one other heteroatom which can be N, O, or S, of which the N can be further substituted with $Y_2$, where $Y_2$ is alkyl, aryl, heteroaryl, aralkyl, heteroaralkyl, alkanoyl, aroyl, heteroaroyl, aralkanoyl, heteroaralkanoyl, alkylsulfonyl, arylsulfonyl, heteroarylsulfonyl, aralkylsulfonyl, heteroaralkylsulfonyl, alkoxycarbonyl, aryloxycarbonyl, heteroaryloxycarbonyl, aralkoxycarbonyl, heteroaralkoxycarbonyl, alkylaminocarbonyl, arylaminocarbonyl, heteroarylaminocarbonyl, aralkylaminocarbonyl, or heteroaralkylaminocarbonyl, in which the alkyl portions can be cyclic and can contain from 1 to 3 heteroatoms which can be N, O, or S;
(3) if the bond between $C_2$ and $N_3$ is a single bond, then the bond between $C_2$ and $R_2$ is a double bond, $R_2$ is O or S, and $R_3$ is hydrogen or alkyl;
(4) if the bond between $C_2$ and $N_3$ is a double bond, then the bond between $C_2$ is a single bond, $R_3$ is not present, and $R_2$ is hydrogen, alkyl, aralkyl, cycloalkyl, heteroaralkyl, halo, amino, $OQ_1$, $SQ_1$, $NHNH_2$, $NHOQ_1$, $NQ_1Q_2$, or $NHQ_1$, where $Q_1$ and $Q_2$ are alkyl, aralkyl, heteroaralkyl, aryl, heteroaryl, alkanoyl, aroyl, aralkanoyl, heteroaralkanoyl, heteroaroyl, alkylsulfonyl, arylsulfonyl, heteroarylsulfonyl, aralkylsulfonyl, or heteroaralkylsulfonyl, in which the alkyl portions can be cyclic and can contain from 1 to 3 heteroatoms which can be N, O, or S, and when $Q_1$ and $Q_2$ are present together and are alkyl, they can be taken together to form a 5- or 6-membered ring which can contain one other heteroatom which can be N, O, or S, of which the N can be further substituted with $Y_2$, where $Y_2$ is alkyl, aryl, heteroaryl, aralkyl, heteroaralkyl, alkanoyl, aroyl, heteroaroyl, aralkanoyl, heteroaralkanoyl, alkylsulfonyl, arylsulfonyl, heteroarylsulfonyl, aralkylsulfonyl, heteroaralkylsulfonyl, alkoxycarbonyl, aryloxycarbonyl, heteroaryloxycarbonyl, aralkoxycarbonyl, heteroaralkoxycarbonyl, alkylaminocarbonyl, arylaminocarbonyl, heteroarylaminocarbonyl, aralkylaminocarbonyl, or heteroaralkylaminocarbonyl, in which the alkyl portions can be cyclic and can contain from 1 to 3 heteroatoms which can be N, O, or S;

(5) $A_7$ and $A_8$ are C or N;
  (a) if $A_7$ and $A_8$ are both C and the bond between $A_7$ and $A_8$ is a single bond, then the bond between $A_8$ and $R_8$ is two single bonds to two hydrogen atoms or is a double bond in which $R_8$ is O or S and $R_7$ is two hydrogen atoms;
  (b) if $A_7$ and $A_8$ are both C and the bond between $A_7$ and $A_8$ is a double bond, then $R_7$ is hydrogen, the bond between $A_8$ and $R_8$ is a single bond and $R_8$ is hydrogen, halo, alkyl, alkenyl, aryl, aralkyl, aralkenyl, heteroaryl, heteroaralkyl, or heteroaralkenyl;
  (c) if $A_7$ and $A_8$ are both N, then the bond between $A_7$ and $A_8$ is a double bond, and $R_7$ and $R_8$ are not present;
  (d) if $A_7$ is C and $A_8$ is N, then the bond between $A_7$ and $A_8$ is a double bond, $R_7$ is hydrogen, and $R_8$ is not present;
  (e) if $A_7$ is N, $A_8$ is C, and the bond between $A_7$ and $A_8$ is a double bond, then $R_7$ is not present, the bond between $A_8$ is a single bond, and $R_8$ is hydrogen, halo, alkyl, alkenyl, aryl, aralkyl, aralkenyl, heteroaryl, heteroaralkyl, or heteroaralkenyl;
  (f) if $A_7$ is N, $A_8$ is C, and the bond between $A_7$ and $A_8$ is a single bond, then $R_7$ is hydrogen, alkyl, aryl, aralkyl, heteroaryl, or heteroaralkyl, the bond between $A_8$ and $R_8$ is a double bond, and $R_8$ is O or S; and (6) $N_9$ is bonded to L; with the proviso that A does not have the structure of an unsubstituted guanine or hypoxanthine.

The purine moiety can be a purine moiety of formula (XI)

in which:
(1) $R_1$ is selected from the group consisting of hydrogen, alkyl, aralkyl, cycloalkyl, and heteroaralkyl; and
(2) $R_2$ is selected from the group consisting of hydrogen, alkyl, aralkyl, cycloalkyl, heteroaralkyl, halo, $OQ_1$, $SQ_1$, $NHNH_2$, $NHOQ_1$, $NQ_1Q_2$, or $NHQ_1$, where $Q_1$ and $Q_2$ are alkyl, aralkyl, heteroaralkyl, aryl, heteroaryl, alkanoyl, aroyl, aralkanoyl, heteroaralkanoyl, heteroaroyl, alkylsulfonyl, arylsulfonyl, heteroarylsulfonyl, aralkylsulfonyl, or heteroaralkylsulfonyl in which the alkyl portions can be cyclic and can contain from 1 to 3 heteroatoms which can be N, O, or S, and when $Q_1$ and $Q_2$ are present together and are alkyl, they can be taken together to form a 5- or 6-membered ring which can contain one other heteroatom which can be N, O, or S, of which the N can be further substituted with $Y_2$, where $Y_2$ is alkyl, aryl, heteroaryl, aralkyl, heteroaralkyl, alkanoyl, aroyl, heteroaroyl, aralkanoyl, heteroaralkanoyl, alkylsulfonyl, arylsulfonyl, heteroarylsulfonyl, aralkylsulfonyl, heteroaralkylsulfonyl, alkoxycarbonyl, aryloxycarbonyl, heteroaryloxycarbonyl, arylkoxycarbonyl, heteroarylokoxycarbonyl, alkylaminocarbonyl, arylaminocarbonyl, heteroarylaminocarbonyl, aralkylaminocarbonyl, or heteroarylkylaminocarbonyl in which the alkyl portions could be cyclic and can contain from one to three heteroatoms which could be N, O, or S, with the proviso that both $R_1$ and $R_2$ are not hydrogen and that $R_1$ is not hydrogen when $R_2$ is amino.

The purine moiety of formula (XI) is a hypoxanthine or a guanine derivative but excludes unsubstituted hypoxanthine, in which $R_1$ and $R_2$ are hydrogen, and unsubstituted guanine, in which $R_1$ is hydrogen and $R_2$ is amino.

In one particularly preferred embodiment, $R_1$ is butyl and $R_2$ is hydrogen.

In another preferred embodiment, $R_1$ is benzyl and $R_2$ is hydrogen.

In another preferred embodiment, $R_1$ is dimethylaminoethyl and $R_2$ is hydrogen.

In another preferred embodiment, $R_1$ is cyclopentyl and $R_2$ is hydrogen.

In another preferred embodiment, $R_1$ is cyclohexylmethyl and $R_2$ is hydrogen.

In another preferred embodiment, $R_1$ is cyclopropylmethyl and $R_2$ is hydrogen.

In another preferred embodiment, $R_1$ is hydrogen and $R_2$ is phenyl.

In another preferred embodiment, $R_1$ is hydrogen and $R_2$ is trifluoromethyl.

In another preferred embodiment, $R_1$ is hydrogen and $R_2$ is butyl.

In another preferred embodiment, $R_1$ is butyl and $R_2$ is butyl.

In another preferred embodiment, $R_1$ is hydrogen and $R_2$ is methyl.

In another preferred embodiment, $R_1$ is hydrogen and $R_2$ is phenylamino.

Alternatively, the purine moiety is a purine moiety of Formula (XII)

in which:
(1) $R_2$ is selected from the group consisting of hydrogen, halo, amino, $OQ_3$, $SQ_3$, $NHNH_2$, $NHOQ_3$, $NQ_3Q_4$, or $NHQ_3$, where $Q_3$ and $Q_4$ are alkyl, aralkyl, heteroaralkyl, aryl, heteroaryl, alkanoyl, aroyl, aralkanoyl, heteroaralkanoyl, heteroaroyl, alkylsulfonyl, arylsulfonyl, heteroarylsulfonyl, aralkylsulfonyl, and heteroaralkylsulfonyl in which the alkyl portions can be cyclic and can contain from 1 to 3 heteroatoms which can be N, O, or S, and when $Q_3$ and $Q_4$ are present together and are alkyl, they can be taken together to form a 5- or 6-membered ring which can contain one other heteroatom which can be N, O, or S, of which the N can be further substituted with $Y_3$ where $Y_3$ is alkyl, aryl, heteroaryl, aralkyl, heteroaralkyl, alkanoyl, aroyl, heteroaroyl, aralkanoyl, heteroaralkanoyl, alkylsulfonyl, arylsulfonyl, heteroarylsulfonyl, aralkylsulfonyl, heteroaralkylsulfonyl, alkoxycarbonyl, aryloxycarbonyl, heteroaryloxycarbonyl, aralkoxycarbonyl, heteroaryloxycarbonyl, alkylaminocarbonyl, arylaminocarbonyl, heteroarylaminocarbonyl, aralkylaminocarbonyl, or heteroaralkylaminocarbonyl, in which the alkyl portions can be cyclic and can contain from 1 to 3 heteroatoms which can be N, O, or S; and (2) $R_6$ is selected from the group consisting of hydrogen, halo, amino, $OQ_5$, $SQ_5$, $NHNH_2$, $NHOQ_5$, $NQ_5Q_6$, or $NHQ_6$, where $Q_5$ and $Q_6$ are alkyl, aralkyl, heteroaralkyl, aryl, heteroaryl, alkanoyl, aroyl, aralkanoyl, heteroaralkanoyl, heteroaroyl, alkylsulfonyl, arylsulfonyl, heteroarylsulfonyl, aralkylsulfonyl, and heteroaralkylsulfonyl in which the alkyl portions can be cyclic and can contain from 1 to 3 heteroatoms which can be N, O, or S, and when $Q_5$ and $Q_6$ are present together and are alkyl, they can be taken together to form a 5- or 6-membered ring which can contain one other heteroatom which can be N, O, or S, of which the N can be further substituted with $Y_2$, where $Y_2$ is alkyl, aryl, heteroaryl, aralkyl, heteroaralkyl, alkanoyl, aroyl, heteroaroyl, aralkanoyl, heteroaralkanoyl, alkylsulfonyl, arylsulfonyl, heteroarylsulfonyl, heteroarylsulfonyl, aralkylsulfonyl, heteroaralkylsulfonyl, alkoxycarbonyl, aryloxycarbonyl, heteroaryloxycarbonyl, arylkoxycarbonyl, heteroarylkoxycarbonyl, alkylaminocarbonyl, arylaminocarbonyl, heteroarylaminocarbonyl, aralkylaminocarbonyl, or heteroaralkylaminocarbonyl in which the alkyl portions can be cyclic and can contain from 1 to 3 heteroatoms which can be N, O, or S.

In one preferred example of this embodiment, $R_2$ is hydrogen and $R_6$ is $-NH_2$ or $-N(CH_3)_2$.

In another preferred example of this embodiment, $R_2$ is hydrogen and $R_6$ is Cl.

In yet another preferred example of this embodiment, $R_2$ is $-NH_2$ and $R_6$ is Cl.

In another alternative, the purine moiety is the purine moiety of Formula (XIII)

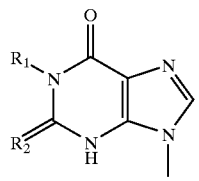

in which:
(1) $R_1$ is hydrogen, alkyl, aralkyl, cycloalkyl, or heteroaralkyl; and
(2) $R_2$ is O or S.

Preferably, in this embodiment, $R_1$ is hydrogen and $R_2$ is O or S.

Particularly preferred purine-based compounds for use in methods according to the present invention include: (1) 4-[3-(1-benzyl-6-oxo-1,6-dihydropurin-9-yl)propionylamino]benzoic acid ethyl ester; (2) 4-[3-(1-butyl-6-oxo-1,6-dihydropurin-9-yl)propionylamino]benzoic acid ethyl ester; (3) 4-[3-(1-methyl-6-oxo-1,6-dihydropurin-9-yl)propionylamino]benzoic acid ethyl ester; (4) 4-[3-(1-(2-dimethylaminoethyl)-6-oxo-1,6-dihydropurin-9-yl)propionylamino]benzoic acid ethyl ester; (5) 4-[3-(2,6-dioxo-1,2,3,6-tetrahydropurin-9-yl)propionylamino]benzoic acid ethyl ester; (6) 4-[3-(6-methoxypurin-9-yl)propionylamino]benzoic acid ethyl ester; (7) 4-[3-(6-dimethylaminopurin-9-yl)propionylamino]benzoic acid ethyl ester; (8) 4-[3-(2-amino-6-chloropurin-9-yl)propionylamino]benzoic acid ethyl ester; (9) 4-[2-(6-oxo-2-thioxo-1,2,3,6-tetrahydropurin-9-yl)propionylmino]benzoic acid ethyl ester; (10) 4-[2-(2-butyl-6-oxo-1,6-dihydropurin-9-yl)propionylamino]benzoic acid ethyl ester; (11) 4-[2-(6-oxo-2-phenyl-1,6-dihydropurin-9-yl)propionylamino] benzoic acid ethyl ester; (12) 4-{[3-(6-chloropurin-9-yl)propionyl]methylamino} benzoic acid methyl ester; (13) 3-(1-benzyl-6-oxo-1,6-dihydropurin-9-yl)-N-[3-(2-oxopyrrolidin-1-yl)propyl]propionamide; (14) 3-(1-benzyl-6-oxo-1,6-dihydropurin-9-yl)-N-{2-[2-(2-oxopyrrolidin-1-yl)acetylamino]ethyl}propionamide; (15) N-3-(2-oxopyrrolidin-1-yl)propyl]-3-(6-oxo-2-thioxo-1,2,3,6-tetrahydropurin-9-yl) propionamide; and (16) 3-(1-benzyl-6-oxo-1,6-dihydropurin-9-yl)-N-(3-mopholin-4-yl-propyl) propionamide.

In another alternative of methods according to the present invention, the compound is a tetrahydroindolone derivative or analogue where A is a 9-atom bicyclic moiety in which the 5-membered ring has one to three nitrogen atoms, the bicyclic moiety having the structure of formula (XIV)

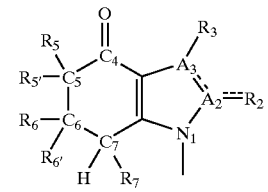

where:
(1) $N_1$ is bonded to L;
(2) $A_2$ and $A_3$ are C or N;
    (a) If $A_2$ and $A_3$ are both C and the bond between $A_2$ and $A_3$ is a single bond, then the bond between $A_2$ and $R_2$ is two single bonds, two hydrogen atoms or is a double bond in which $R_2$ is O or S and $R_3$ is two hydrogen atoms;
    (b) If $A_2$ and $A_3$ are both C and the bond between $A_2$ and $A_3$ is a double bond, then $R_3$ is hydrogen, the bond between $A_2$ and $R_2$ is a single bond and $R_2$ is hydrogen, halo, alkyl, alkenyl, aryl, aralkyl, aralkenyl, heteroaryl, heteroaralkyl, or heteroaralkenyl;
    (c) If $A_2$ and $A_3$ are both N, then the bond between $A_2$ and $A_3$ is a double bond and $R_2$ and $R_3$ are not present;
    (d) If $A_2$ is N and $A_3$ is C, then the bond between $A_2$ and $A_3$ is a double bond, $R_2$ is not present, and $R_3$ is hydrogen;
    (e) If $A_2$ is C, $A_3$ is N, and the bond between $A_2$ and $A_3$ is a double bond, then $R_3$ is not present, the bond between $A_2$ and $R_2$ is a single bond, and $R_2$ is hydrogen, halo, alkyl, alkenyl, aryl, aralkyl, aralkenyl, heteroaryl, heteroaralkyl, or heteroaralkenyl;

(f) If $A_2$ is C, $A_3$ is N, and the bond between $A_2$ and $A_3$ is a single bond, then $R_3$ is hydrogen, alkyl, aryl, aralkyl, heteroaryl, or heteroaralkenyl, the bond between $A_2$ and $R_2$ is a double bond, and $A_2$ is O or S;

(3) $R_5$ is hydrogen, alkyl, aryl, aralkyl, heteroaryl, heteroaralkyl, alkanoyl, aroyl, heteroaroyl, aralkanoyl, heteroaralkanoyl, $NH_2$, $NHQ_1$, $NQ_1Q_2$, OH, $OQ_1$, or $SQ_1$, where $Q_1$ and $Q_2$ are alkyl, aralkyl, heteroaralkyl, aryl, heteroaryl, alkanoyl, aroyl, aralkanoyl, heteroaralkanoyl, heteroaroyl, alkylsulfonyl, arylsulfonyl, heteroarylsulfonyl, aralkylsulfonyl, or heteroaralkylsulfonyl in which the alkyl portions can be cyclic and can contain from 1 to 3 heteroatoms which can be N, O, or S, of which the N can be further substituted with $Y_2$, where $Y_2$ is alkyl, aryl, heteroaryl, aralkyl, heteroaralkyl, alkanoyl, aroyl, heteroaroyl, aralkanoyl, heteroaralkanoyl, alkylsulfonyl, arylsulfonyl, heteroarylsulfonyl, aralkylsulfonyl, or heteroaralkylsulfonyl, in which the alkyl portions can be cyclic and can contain from 1 to 3 heteroatoms which can be N, O, or S, and when $Q_1$ and $Q2$ are present together and are alkyl, they can be taken together to form a 5- or 6-membered ring which can contain one other heteroatom, which can be N, O, or S, of which the N can be further substituted with $Y_2$, where $Y_2$ is alkyl, aryl, heteroaryl, aralkyl, heteroaralkyl, alkanoyl, aroyl, heteroaroyl, aralkanoyl, heteroaralkanoyl, alkylsulfonyl, arylsulfonyl, heteroarylsulfonyl, aralkylsulfonyl, heteroaralkylsulfonyl, alkoxycarbonyl, aryloxycarbonyl, heteroaryloxycarbonyl, aralkoxycarbonyl, heteroaralkoxycarbonyl, alkylaminocarbonyl, arylaminocarbonyl, heteroarylaminocarbonyl, aralkylaminocarbonyl, or heteroaralkylaminocarbonyl, in which the alkyl portions can be cyclic and can contain from 1 to 3 heteroatoms which can be N, O, or S;

(4) $R_{5'}$ is hydrogen unless $R_5$ is alkyl, in which case $R_{5'}$ is hydrogen or the same alkyl as $R_5$;

(5) $R_5$ and $R_{5'}$ can be taken together as a double bond to $C_5$, and can be O, S, $NQ_3$, or C which can be substituted with one or two groups $R_5$, where $Q_3$ is alkyl, aralkyl, heteroaralkyl, aryl, heteroaryl, alkanoyl, aroyl, aralkanoyl, heteroaralkanoyl, or heteroaroyl, in which the alkyl portions can be cyclic and can contain from 1 to 3 heteroatoms which can be N, O, or S;

(6) $R_6$ is hydrogen, alkyl, aryl, aralkyl, heteroaryl, heteroaralkyl, $NH_2$, $NHQ_4$, $NQ_4Q_5$, OH, $OQ_4$, or $SQ_4$, where $Q_4$ and $Q_5$ are alkyl, aralkyl, heteroaralkyl, aryl, heteroaryl, alkanoyl, aroyl, aralkanoyl, heteroaralkanoyl, heteroaroyl, alkylsulfonyl, arylsulfonyl, heteroarylsulfonyl, aralkylsulfonyl, or heteroaralkylsulfonyl in which the alkyl portions can be cyclic and can contain from 1 to 3 heteroatoms which can be N, O, or S, and when $Q_4$ and $Q_5$ are present together and are alkyl, they can be taken together to form a 5- or 6-membered ring which can contain one other heteroatom, which can be N, O, or S, of which the N can be further substituted with $Y_2$, where $Y_2$ is alkyl, aryl, heteroaryl, aralkyl, heteroaralkyl, alkanoyl, aroyl, heteroaroyl, aralkanoyl, heteroaralkanoyl, alkylsulfonyl, arylsulfonyl, heteroarylsulfonyl, aralkylsulfonyl, heteroaralkylsulfonyl, alkoxycarbonyl, aryloxycarbonyl, heteroaryloxycarbonyl, aralkoxycarbonyl, heteroaralkoxycarbonyl, alkylaminocarbonyl, arylaminocarbonyl, heteroarylaminocarbonyl, aralkylaminocarbonyl, or heteroaralkylaminocarbonyl, in which the alkyl portions can be cyclic and can contain from 1 to 3 heteroatoms which can be N, O, or S;

(7) $R_{6'}$ is hydrogen unless $R_6$ is alkyl, in which case $R_{6'}$ is hydrogen or the same alkyl as $R_6$;

(8) $R_6$ and $R_{6'}$ can be taken together as a double bond to $C_6$ and can be O, S, $NQ_6$, or C which can be substituted with one or two groups $R_5$, and where $Q_6$ is alkyl, aralkyl, heteroaralkyl, aryl, heteroaryl, alkanoyl, aroyl, aralkanoyl, heteroaralkanoyl, heteroaroyl, alkylsulfonyl, arylsulfonyl, heteroarylsulfonyl, aralkylsulfonyl, or heteroaralkylsulfonyl, in which the alkyl portions can be cyclic and can contain from 1 to 3 heteroatoms which can be N, O, or S; and (9) $R_7$ is hydrogen unless $R_5$ is alkyl and $R_{5'}$ is hydrogen, in which case $R_7$ is the same alkyl as $R_5$.

Typically, A is a tetrahydroindolone moiety. More typically, the tetrahydroindolone moiety is a tetrahydroindolone moiety of formula (XV)

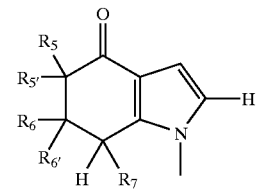

in which:

(1) $R_5$ is hydrogen, alkyl, aryl, aralkyl, heteroaryl, heteroaralkyl, alkanoyl, aroyl, heteroaroyl, aralkanoyl, heteroaralkanoyl, $NH_2$, $NH_1$, $NQ_1Q_2$, OH, $OQ_1$, or $SQ_1$, where $Q_1$ and $Q_2$ are alkyl, aralkyl, heteroaralkyl, aryl, heteroaryl, alkanoyl, aroyl, aralkanoyl, heteroaralkanoyl, or heteroaroyl, in which the alkyl portions can be cyclic and can contain from one to three heteroatoms which can be N, O, or S;

(2) $R_5$ is hydrogen;

(3) $R_6$ is hydrogen, alkyl, aryl, aralkyl, heteroaryl, heteroaralkyl, alkanoyl, aroyl, heteroaroyl, aralkanoyl, heteroaralkanoyl, $NH_2$, $NHW_1$, $NQ_1Q_2$, OH, $OQ_1$, or $SQ_1$, where $Q_1$ and $Q_2$ are aralkyl, heteroaralkyl, aryl, heteroaryl, alkanoyl, aroyl, aralkanoyl, heteroaralkanoyl, or heteroaroyl, in which the alkyl portions can be cyclic and can contain from one to three heteroatoms which can be N, O, or S and where $W_1$ is alkyl, aralkyl, heteroaralkyl, aryl, heteroaryl, alkanoyl, aroyl, aralkanoyl, heteroaralkanoyl, heteroaroyl, alkylsulfonyl, arylsulfonyl, heteroarylsulfonyl, aralkylsulfonyl, or heteroaralkylsulfonyl, in which the alkyl portions can be cyclic and can contain from one to three heteroatoms which can be N, O, or S;

(4) $R_{6'}$ is hydrogen; and (5) $R_7$ is hydrogen.

Typically, $R_5$, $R_{5'}$, $R_6$, $R_{6'}$, and $R_7$ are all hydrogen.

When A is a tetrahydroindolone moiety, preferred compounds are 4-[3-(4-oxo-4,5,6,7-tetrahydroindolon-1-yl) propionylamino]benzoic acid ethyl ester and 4-[3-(4-oxo-4,5,6,7-tetrahydroindolon-1-yl) propionylamino]benzoic acid.

In another alternative, the compound is a pyrimidine derivative or pyrimidine analogue. In this alternative, A is an amino-substituted 6-membered heterocyclic moiety of formula (XVI)

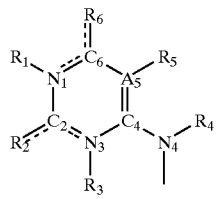

where:
(1) if the bond between $N_1$ and the bond between $C_6$ is a single bond, then the bond between $C_6$ and $R_6$ is a double bond, $R_6$ is O or S, and $R_1$ is hydrogen, alkyl aralkyl, cycloalkyl, or heteroaralkyl;

(2) if the bond between $N_1$ and $C_6$ is a double bond, then the bond between $C_6$ and $R_6$ is a single bond, $R_1$ is not present, and $R_6$ is hydrogen, halo, amino, OH, $OQ_1$, $SQ_1$, $NHNH_2$, $NQ_1Q_2$, or $NHQ_1$, where $Q_1$ and $Q_2$ are alkyl, aralkyl, heteroaralkyl, aryl, heteroaryl, alkanoyl, aroyl, aralkanoyl, heteroaralkanoyl, heteroaroyl, alkylsulfonyl, arylsulfonyl, heteroarylsulfonyl, aralkylsulfonyl, or heteroaralkylsulfonyl in which the alkyl portions can be cyclic and can contain from 1 to 3 heteroatoms which can be N, O, or S, and when $Q_1$ and $Q_2$ are present together and are alkyl, they can be taken together to form a 5- or 6-membered ring which can contain one other heteroatom which can be N, O, or S, of which the N can be further substituted with $Y_2$, where $Y_2$ is alkyl, aryl, heteroaryl, aralkyl, heteroaralkyl, alkanoyl, aroyl, heteroaroyl, aralkanoyl, heteroaralkanoyl, alkylsulfonyl, arylsulfonyl, heteroarylsulfonyl, aralkylsulfonyl, heteroaralkylsulfonyl, alkoxycarbonyl, aryloxycarbonyl, heteroaryloxycarbonyl, aralkoxycarbonyl, heteroaralkoxycarbonyl, alkylaminocarbonyl, arylaminocarbonyl, heteroarylaminocarbonyl, aralkylaminocarbonyl, or heteroaralkylaminocarbonyl, in which the alkyl portions can be cyclic and can contain from 1 to 3 heteroatoms which can be N, O, or S;

(3) if the bond between $C_2$ and $N_3$ is a single bond, then the bond between $C_2$ and $R_2$ is a double bond, $R_2$ is O or S, and $R_3$ is hydrogen or alkyl;

(4) if the bond between $C_2$ and $N_3$ is a double bond, then the bond between $C_2$ and $R_2$ is a single bond, $R_3$ is not present, and $R_2$ is hydrogen, alkyl, aralkyl, cycloalkyl, heteroaralkyl, halo, amino, OH, $OQ_1$, $SQ_1$, $NHNH_2$, $NHOQ_1$, $NQ_1Q_2$, or $NHQ_1$, where $Q_1$ and $Q_2$ are alkyl, aralkyl, heteroaralkyl, aryl, heteroaryl, alkanoyl, aroyl, aralkanoyl, heteroaralkanoyl, heteroaroyl, alkylsulfonyl, arylsulfonyl, heteroarylsulfonyl, aralkylsulfonyl, or heteroaralkylsulfonyl, in which the alkyl portions can be cyclic and can contain from 1 to 3 heteroatoms which can be N, O, or S, and when $Q_1$ and $Q_2$ are present together and are alkyl, they can be taken together to form a 5- or 6-membered ring which can contain one other heteroatom which can be N, O, or S, of which the N can be further substituted with $Y_3$, where $Y_3$ is alkyl, aryl, heteroaryl, aralkyl, heteroaralkyl, alkanoyl, aroyl, heteroaroyl, aralkanoyl, heteroaralkanoyl, alkylsulfonyl, arylsulfonyl, heteroarylsulfonyl, aralkylsulfonyl, heteroaralkylsulfonyl, alkoxycarbonyl, aryloxycarbonyl, heteroaryloxycarbonyl, aralkoxycarbonyl, heteroaralkoxycarbonyl, alkylaminocarbonyl, arylaminocarbonyl, heteroarylaminocarbonyl, aralkylaminocarbonyl, or heteroaralkylaminocarbonyl, in which the alkyl portions can be cyclic and can contain from 1 to 3 heteroatoms which can be N, O, or S;

(5) $R_4$ is hydrogen, alkyl, aralkyl, heteroaralkyl, alkanoyl, aroyl, heteroaroyl, aralkanoyl, heteroaralkanoyl, alkylsulfonyl, arylsulfonyl, heteroarylsulfonyl, alkoxycarbonyl, aryloxycarbonyl, heteroaryloxycarbonyl, alkylaminocarbonyl, arylaminocarbonyl, or heteroarylaminocarbonyl;

(6) $A_5$ is carbon or nitrogen;

(7) if $A_5$ is nitrogen, then $R_5$ is not present;

(8) if $A_5$ is carbon, then $R_5$ is hydrogen, amino, alkyl, alkoxy, halo, nitro, aryl, cyano, alkenyl, or alkaryl;

(9) if $R_5$ and $R_6$ are present together and are alkyl, they can be taken together to form a 5- or 6-membered ring which can contain one other heteroatom which can be N, O, or S, of which the N can be further substituted with $Y_2$, where $Y_2$ is alkyl, aryl, heteroaryl, aralkyl, heteroaralkyl, alkanoyl, aroyl, heteroaroyl, aralkanoyl, heteroaralkanoyl, alkylsulfonyl, arylsulfonyl, heteroarylsulfonyl, aralkylsulfonyl, heteroaralkylsulfonyl, alkoxycarbonyl, aryloxycarbonyl, heteroaryloxycarbonyl, aralkoxycarbonyl, heteroaralkoxycarbonyl, alkylaminocarbonyl, arylaminocarbonyl, heteroarylaminocarbonyl, aralkylaminocarbonyl, or heteroaralkylaminocarbonyl, in which the alkyl portions can be cyclic and can contain from 1 to 3 heteroatoms which can be N, O, or S; and

(10) $N_4$ is bonded to L.

Typically, $A_5$ is carbon and the 6-membered heterocyclic moiety is a pyrimidine moiety.

When A is a pyrimidine moiety, in one alternative, $R_2$ is O and $R_3$ is hydrogen. In this alternative, the pyrimidine moiety can be cytosine, thymine, uracil, 3-methyluracil, 3-methylthymine, 4-methylcytosine, 5-methylcytosine, 5-hydroxymethylcytosine, 5-hydroxyuracil, 5-carboxymethyluracil, or 5-hydroxymethyluracil.

In another alternative, $R_2$ is S and $R_3$ is hydrogen. In this alternative, the pyrimidine moiety can be 2-thiouracil, 5-methylamino-2-thiouracil, 5-methyl-2-thiouracil, or 2-thiocytosine.

In still another alternative, $R_2$ is amino and the bond between $C_2$ and $N_3$ is a double bond. In this alternative, the pyrimidine moiety can be 2-aminopyrimidinone or 2-amino-4-chloropyrimidine.

In still another alternative, $R_2$ is hydrogen and the bond between $C_2$ and $N_3$ is a double bond. In this alternative, the pyrimidine moiety can be 4-chloropyrimidine, 5-amino-4-chloropyrimidine, 4-chloro-5-methylpyrimidine, 4-chloro-5-hydroxymethylpyrimidine, or 4-chloro-5-carboxymethylpyrimidine.

In still another alternative, $R_1$ is hydrogen, methyl, or ethyl, $R_5$ is hydrogen, methyl, or ethyl, and $R_6$ is O. In this alternative, the pyrimidine moiety can be pyrimidinone.

Particularly preferred pyrimidine compounds include. 4-[3-(2-amino-6-chloropyrimidin-4-ylamino) propionylamino]benzoic acid ethyl ester; 4-[3-(5-amino-6-chloropyrimidin-4-ylamino) propionylamino]benzoic acid ethyl ester; 4-[3-(6-chloropyrimidin-4-ylamino) propionylamino]benzoic acid ethyl ester; 4-[3-(2-amino-6-chloropyrimidin-4-ylamino) propionylamino]benzoic acid; 4-[3-(6-chloropyrimidin-4-ylamino) propionylamino]

benzoic acid; 4-[3-(5-amino-6-chloropyrimidin-4-ylamino) propionylamino]benzoic acid; 3-[3-(2-amino-6-chloropyrimidin-4-ylamino) propionylamino]benzoic acid ethyl ester; 3-[3-(6-chloropyrimidin-4-ylamino) propionylamino]benzoic acid ethyl ester; 3-[3-(5-amino-6-chloropyrimidin-4-ylamino) propionylamino]benzoic acid ethyl ester; 3-[3-(2-amino-6-chloropyrimidin-4-ylamino) propionylamino]benzoic acid; 3-[3-(6-chloropyrimidin-4-ylamino) propionylamino]benzoic acid; and 3-[3-(5-amino-6-chloropyrimidin-4-ylamino) propionylamino]benzoic acid.

In accordance with the present invention, and as used herein, the following terms, when appearing alone or as part of a moiety including other atoms or groups, are defined with the following meanings, unless explicitly stated otherwise. In addition, all groups described herein can be optionally substituted unless such substitution is excluded. The term "alkyl," as used herein at all occurrences, refers to saturated aliphatic groups including straight-chain, branched-chain, and cyclic groups, all of which can be optionally substituted. Preferred alkyl groups contain 1 to 10 carbon atoms. Suitable alkyl groups include methyl, ethyl, and the like, and can be optionally substituted. The term "alkenyl," as used herein at all occurrences, refers to unsaturated groups which contain at least one carbon-carbon double bond and includes straight-chain, branched-chain, and cyclic groups, all of which can be optionally substituted. Preferable alkenyl groups have 2 to 10 carbon atoms. The term "alkoxy" refers to the ether —O-alkyl, where alkyl is defined as as above. The term "aryl" refers to aromatic groups which have at least one ring having a conjugated π-electron system and includes carbocyclic aryl and biaryl, both of which may be optionally substituted. Preferred aryl groups have 6 to 10 carbon atoms. The term "aralkyl" refers to an alkyl group substituted with an aryl group. Suitable aralkyl groups include benzyl and the like; these groups can be optionally substituted. The term "aralkenyl" refers to an alkenyl group substituted with an aryl group. The term "heteroaryl" refers to carbon-containing 5–14 membered cyclic unsaturated radicals containing one, two, three, or four O, N, or S heteroatoms and having 6, 10, or 14π-electrons delocalized in one or more rings, e.g., pyridine, oxazole, indole, thiazole, isoxazole, pyrazole, pyrrole, each of which can be optionally substituted as discussed above. The term "sulfonyl" refers to the group —S(O$_2$)—. The term "alkanoyl" refers to the group —C(O)Rg, where Rg is alkyl. The term "aroyl" refers to the group —C(O)Rg, where Rg is aryl. Similar compound radicals involving a carbonyl group and other groups are defined by analogy. The term "aminocarbonyl" refers to the group —NHC(O)—. The term "oxycarbonyl" refers to the group —OC(O)—. The term "heteroaralkyl" refers to an alkyl group substituted with a heteroaryl group. Similarly, the term "heteroaralkenyl" refers to an alkenyl group substituted with a heteroaryl group. As used herein, the term "lower," in reference to an alkyl or the alkyl portion of an another group including alkyl, is defined as a group containing one to six carbon atoms. The term "optionally substituted" refers to one or more substituents that can be lower alkyl, aryl, amino, hydroxy, lower alkoxy, aryloxy, lower alkylamino, arylamino, lower alkylthio, arylthio, or oxo, in some cases, other groups can be included, such as cyano, acetoxy, or halo. The term "halo" refers generally to fluoro, chloro, bromo, or iodo; more typically, "halo" refers to chloro.

As indicated above, the linker L is a hydrocarbyl moiety of 1 to 6 carbon atoms that can be cyclic, with the hydrocarbyl moiety being optionally substituted with one or more substituents selected from the group consisting of lower alkyl, amino, hydroxy, lower alkoxy, lower alkylamino, lower alkylthio, and oxo. Preferably, the linker L has the structure —(CH$_2$)$_n$— wherein n is an integer from 1 to 6. As detailed below, for most preferred embodiments of compounds useful in methods according to the present invention, a preferred linker has n equal to 2 or 3.

The moiety B is either: (i) —OZ, where Z is hydrogen, alkyl, aryl, heteroaryl, cycloalkyl, aralkyl, or heteroaralkyl; or (ii) N(Y$_1$)—D, where D is a moiety that promotes absorption of the compound, and Y$_1$ is hydrogen, alkyl, aryl, heteroaryl, aralkyl, heteroaralkyl, which, when taken with D, can form a cyclic 5- or 6-membered saturated ring which can contain one other heteroatom which can be O, N, or S, of which N can be further substituted with Y$_2$, where Y$_2$ is alkyl, aryl, heteroaryl, aralkyl, heteroaralkyl, alkanoyl, aroyl, heteroaroyl, aralkanoyl, heteroaralkanoyl, alkylsulfonyl, arylsulfonyl, heteroarylsulfonyl, aralkylsulfonyl, heteroaralkylsulfonyl, alkoxycarbonyl, aryloxycarbonyl, heteroaryloxycarbonyl, aralkoxycarbonyl, heteroaralkoxycarbonyl, alkylaminocarbonyl, arylaminocarbonyl, heteroarylaminocarbonyl, aralkylaminocarbonyl, heteroaralkylaminocarbonyl, in which the alkyl portions can be cyclic and can contain from 1 to 3 heteroatoms which can be N, O, or S. Typically, Y$_1$ is hydrogen. Where the moiety B is —OZ, the moiety B is a carboxylic acid or carboxylic acid or ester. Typically, where B is a carboxylic acid ester, the moiety Z is a lower alkyl, such as methyl, ethyl, butyl, propyl, or isopropyl.

In one alternative, the moiety D, as described above, is a moiety having at least one polar, charged, or hydrogen-bond-forming group to improve the metabolic and bioavailability properties of the compound. The moiety D can be, but is not limited to, a moiety with physiological or biological activity such as nootropic activity. In one alternative, the moiety D can be a moiety containing at least one carboxyl, carboxamide, carboxyl ester, or carbonyl function. In another alternative, the moiety D can be a moiety containing at least one hydroxyl, primary amino, secondary amino, tertiary amino, sulfhydryl, or sulfonamidyl function. The moiety D can be cyclic or acyclic. Preferred examples of the moiety D are described below.

When the moiety D is a cyclic or acyclic moiety containing at least one carbonyl, carboxamide, carboxyl ester, or carbonyl function, in one preferred example, D is a carboxylic acid or carboxylic acid ester with the structure

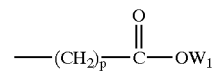

wherein p is an integer from 1 to 6 and W$_1$ is selected from the group consisting of hydrogen and lower alkyl. Typically, if W$_1$ is lower alkyl, it is methyl, ethyl, propyl, butyl, or isobutyl. Typically, p is 3. Typically, W$_1$ is hydrogen or ethyl.

In another preferred example, D and Y$_1$ are taken together to form a piperazine derivative as described in D. Manetti et al., "Molecular Simplification of 1,4-Diazabicyclo[4.3.0] nonan-9-ones Gives Piperazine Derivatives That Maintain High Nootropic Activity," *J. Med. Chem.* 43: 4499–4507 ("Manetti et al. (2000)"). B is an analogue of structure

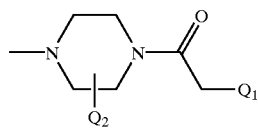

wherein $Q_1$ is hydrogen, methyl, ethyl, butyl, or propyl, $Q_2$ is hydrogen or methyl, where, if $Q_2$ is methyl, it can be located at either of the two possible positions in the piperazine ring.

In another preferred example, D has the structure

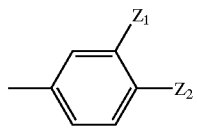

where one of $Z_1$ and $Z_2$ is hydrogen, and the other of $Z_1$ and $Z_2$ is —COOH or —COOW$_1$, wherein W$_1$ is alkyl. Typically, W$_1$ is selected from the group consisting of methyl, ethyl, propyl, butyl, and isobutyl. Either of $Z_1$ or $Z_2$ can be hydrogen. When $Z_1$ is hydrogen and $Z_2$ is —COOH, the moiety B is p-aminobenzoic acid (PABA). When $Z_1$ is —COOH and $Z_2$ is hydrogen, the moiety B is m-aminobenzoic acid (MABA). When $Z_1$ is hydrogen and $Z_2$ is —COOW$_1$, the moiety B is an ester of p-aminobenzoic acid (PABA). When $Z_1$ is —COOW$_1$ and $Z_2$ is hydrogen, the moiety B is an ester of m-aminobenzoic acid (MABA). Typically, these esters are ethyl esters.

When the moiety D is a moiety that contains at least one hydroxyl, primary amino, secondary amino, tertiary amino, sulfhydryl, or sufonamidyl function, in one preferred example, D is a phenylsulfonamidyl moiety of structure

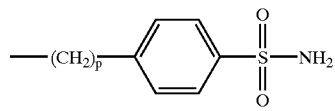

wherein p is an integer from 0 to 6. Typically, p is 2.

In another preferred example, D is an alkylpyridyl moiety of structure

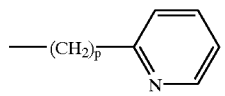

wherein p is an integer from 1 to 6. Typically, p is 1.

In another preferred example, D is a dialkylaminoalkyl moiety of the structure

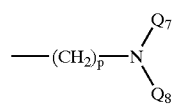

wherein p is an integer from 1 to 6 and $Q_7$ and $Q_8$ are alkyl, aralkyl, heteroaralkyl, aryl, heteroaryl, alkanoyl, aroyl, aralkanoyl, heteroaralkanoyl, or heteroaroyl in which the alkyl portions can be cyclic and can contain from 1 to 3 heteroatoms which can be N, O, or S, and when $Q_1$ and $Q_2$ are present together and are alkyl, they can be taken together to form a 5 or 6 member ring which may contain 1 other heteroatom which can be N, O, or S, of which the N may be further substituted with $Y_2$, where $Y_2$ is alkyl, aryl, heteroaryl, aralkyl, heteroaralkyl, alkanoyl, aroyl, heteroaroyl, aralkanoyl, heteroaralkanoyl, alkylsulfonyl, arylsulfonyl, heteroarylsulfonyl, aralkylsulfonyl, heteroaralkylsulfonyl, alkoxycarbonyl, aryloxycarbonyl, heteroaryloxycarbonyl, aralkoxycarbonyl, heteroaralkoxycarbonyl, alkylaminocarbonyl, arylaminocarbonyl, heteroarylaminocarbonyl, aralkylaminocarbonyl, or heteroaralkylaminocarbonyl, in which the alkyl portions can be cyclic and can contain from 1 to 3 heteroatoms which can be N, O, or S.

Where $Q_7$ and $Q_8$ can be taken together to form a five or six member ring, the ring is typically pyrrolidine, piperidine, or morpholine. The pyrrolidine ring can be optionally substituted with oxo. The piperidine ring can be optionally substituted with methyl or ethyl. Typically, p is 2 or 3.

In another preferred example, D is an alkylpyrrolidine moiety of the structure

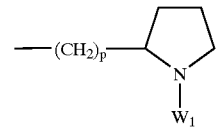

wherein p is an integer from 1 to 6 and $W_1$ is selected from the group consisting of methyl, ethyl, and propyl. Typically, $W_1$ is methyl. Typically, p is 2.

Preferably, a compound useful in methods according to the present invention has a log P of from about 1 to about 4 in order to optimize bioavailability and CNS penetration of the compound.

As detailed below in the Example, compounds used in methods according to the present invention are believed to exert their activity through the upregulation of neurotrophic factor synthesis. The upregulation of neurotrophic factor synthesis can involve one or more of these neurotrophic factors: NGF, NT-3, BDNF, and NT-4/5.

Exemplary studies and treatments were performed as discussed below using various dosages and routes of administration of selected exemplary compounds representative of compositions that are effective with the methods of the present invention. Of course, those skilled in the art will recognize that the present invention is not specifically limited to the particular compositions, dosages or routes of administration detailed below.

Depending upon the particular needs of the individual subject involved, the compositions used in the present invention may be administered in various doses to provide effective treatment concentrations based upon the teachings of the present invention. What constitutes an effective amount of the selected composition will vary based upon such factors including the activity of the selected compound, the physiological characteristics of the subject, the extent and nature of the subject's disease or condition and the method of administration. Exemplary treatment concentrations which have proven effective in modifying neural activity range from less than 1 μM to concentrations of 500 mM or more: Generally, initial doses will be modified to determine the optimum dosage for treatment of the particular mammalian subject. The compositions may be administered using a number of different routes including orally, topically, transdermally, intraperitoneal injection or intravenous injection directly into the bloodstream. Of course, effective amounts of the compounds may also be administered through injection into the cerebrospinal fluid or infusion directly into the brain, if desired.

The methods of the present invention may be effected using compounds administered to a mammalian subject either alone or in combination as a pharmaceutical formulation. Further, the compounds may be combined with pharmaceutically acceptable excipients and carrier materials such as inert solid diluents, aqueous solutions or non-toxic organic solvents. If desired, these pharmaceutical formulations may also contain preservatives and stabilizing agents and the like, as well as minor amounts of auxiliary substances such as wetting or emulsifying agents, as well as pH buffering agents and the like which enhance the effectiveness of the active ingredient. The pharmaceutically acceptable carrier can be chosen from those generally known in the art, including, but not limited to, human serum albumin, ion exchangers, dextrose, alumina, lecithin, buffer substances such as phosphate, glycine, sorbic acid, potassium sorbate, propylene glycol, polyethylene glycol, and salts or electrolytes such as protamine sulfate, sodium chloride, or potassium chloride. Other carriers can be used.

Liquid compositions can also contain liquid phases either in addition to or to the exclusion of water. Examples of such additional liquid phases are glycerin, vegetable oils such as cottonseed oil, organic esters such as ethyl oleate, and water-oil emulsions.

The compositions can be made into aerosol formations (i.e., they can be "nebulized") to be administered via inhalation. Aerosol formulations can be placed into pressurized acceptable propellants, such as dichloromethane, propane, or nitrogen. Other suitable propellants are known in the art.

Formulations suitable for parenteral administration, such as, for example, by intravenous, intramuscular, intradermal, and subcutaneous routes, include aqueous and non-aqueous, isotonic sterile injection solutions. These can contain antioxidants, buffers, preservatives, bacteriostatic agents, and solutes that render the formulation isotonic with the blood of the particular recipient. Alternatively, these formulations can be aqueous or non-aqueous sterile suspensions that can include suspending agents, thickening agents, solubilizers, stabilizers, and preservatives. Compositions suitable for use in methods according to the present invention can be administered, for example, by intravenous infusion, orally, topically, intraperitoneally, intravesically, or intrathecally. Formulations of compounds suitable for use in methods according to the present invention can be presented in unit-dose or multi-dose sealed containers, in physical forms such as ampules or vials.

The drug-induced peripheral neuropathy to be treated can be drug-induced peripheral neuropathy induced by the administration of a vinca alkaloid, cisplatin, paclitaxel, suramin, altretamine, carboplatin, chlorambucil, cytarabine, dacarbazine, docetaxel, etoposide, fludarabine, ifosfamide with mesna, tamoxifen, teniposide, and thioguanine. Vinca alkaloids include vincristine and vinblastine. Peripheral neuropathy associated with the administration of oncolytic drugs is described in C. M. Haskell, "Cancer Treatment" ($5^{th}$ Ed., W.B. Saunders, Philadelphia, 2001), ch. 10, pp. 104–214, incorporated herein by this reference. In particular, methods according to the present invention are particularly useful in treating drug-induced peripheral neuropathy associated with the administration of vincristine, paclitaxel, or cisplatin.

Although Applicants do not intend to be bound by this theory, the beneficial effects of bifunctional purine derivatives such as AIT-082 may depend on generalized trophic and NGF-sensitive mechanisms and not merely on the induction of sprouting. These trophic effects may boost the capacity of NGF-sensitive neurons to respond to still unknown regeneration factors other than NGF itself. For example, it is likely that CGRP and Substance P expression increases with treatment with AIT-082 or other bifunctional purine derivatives.

The invention is illustrated by the following Examples. These Examples are presented for illustration only and are not intended to limit the invention.

EXAMPLE 1

Effect of AIT-082 on Neurotoxicity Induced by Cisplatin and Vincristine

Methods and Materials

In Vitro Procedures

Culture of Dorsal Root Ganglion Neurons.

The dorsal root ganglion neurons were obtained from rat fetuses (Wistar rats; E15; Elevage Janvier, Le Genest St Isle). They were dissected and incubated in trypsin 1× (Gibco; Life Technologies, Cergy-Pontoise, France) for 30 min at 37° C. The reaction was stopped by addition of free Hanks balanced salt solution containing calcium and magnesium; ($HBSS^+$; Gibco) added with 10% of fetal bovine serum (FBS; Gibco) and 0.5 mg/ml DNAse I (Boehringer Mannheim, Meylan, France). The suspension was triturated with a 10-ml pipette and using a needle seringe. After centrifugation, the dissociated cells were resuspended in DMEM containing 10% FBS, 2% of chick embryos extract (Gibco), 1% antibiotics (Gibco) and NGF (Tebu, Le Perray en Yvelines, France) 3 ng/ml final.

Viable cells were counted and seeded at ±50,000 cells /well in 96 well-plates (Nunclon, Life Technologies) coated with poly-L-lysine (0.01 mg/ml, Sigma). Cells were maintained in a humidified incubator at 37° C. in 5% $CO_2$-95% air atmosphere.

After 24 h, the culture medium was completed with anti-mitotic compounds (5-fluoro-5'-deoxyuridine and cytosine β-D-arabinofuranoside) and uridine all $10^{-5}$M final. This treatment is aimed at eliminating contaminating fibroblasts and inhibiting the proliferation of Schwann cells.

Cultures were rinsed 48 hrs later (medium without any growth factors) and medium was replaced with fresh medium (200 μl /well) containing cisplatin (3.5 ng/ml; Sigma) added or not with the reference or test compounds.

After 48 h of intoxication, survival rates were measured using an acid phosphatase enzymatic activity assay.

Survival Rate.

Acid phosphatase activity was measured according to a previously described method (Ueda et al.; 1994). After removal of the culture medium, wells were rinsed twice with PBS (Life Technologies) and incubated with 100 μl of buffer containing 0.1 M sodium acetate (pH5.5), 0.1% Triton X100 (Sigma) and 10 mM p-nitrophenyl phosphate (Sigma) 1 h at 37° C./5% $CO_2$. Reaction was stopped by addition of 10 μl of 1N NaOH (LPCR, Strasbourg, France). Enzyme activity was measured at 405 nm in a microplate reader (Labsystem, France).

Acid phosphatase activity is proportional to the amount of living cells. The results were expressed as percentage O.D. as compared to control conditions (same rinsing and medium replacements, but no intoxication and no treatment with either NGF, riluzol or the test compounds).

In Vivo Procedures

Animals received vincristine 0.15 mg/ml (IP) per day with the following timing: 5 days of intoxication followed with 2 days without vincristine injection and a new period of 5 days of intox followed with 2 days no intoxication and 2 other days of intoxication with vincristine followed by a 3 week recovery period. The test compound was administered daily from the first day of vincristine injection to the end of the experiments Subjects used were 65 female Dark Agouti rats (200–250 g) (n=13 per group). Five groups were used: (1) a vehicle control group; (2) a vincristine-vehicle group;: (3) a vicristine+AIT-082 3 mg/kg IP group; (4) a vicristine+AIT-082 10 mg/kg IP group; and (5) a vicristine+AIT-082 30 mg/kg IP group.

Behavioral Measurements. The general health and weight of animals were checked every day. Sensorimotor tests were performed twice a week during 6 week study, starting one week before beginning of intoxication (baseline).

Electrophysiological Measurements. Electrophysiological recordings were performed once a week using a Neuromatic 2000M electromyographical apparatus (Dantec, France). EMG were performed under Ketamine anesthesia (Imalgène 500®, Merieux, France).

The measured parameters were: the sensitive nerve conduction velocity (SNCV), the amplitude and the latency compound muscle action potential (CMAP).

Sensitive Nerve Conduction Velocity. Skin electrodes were used. Caudal nerve was stimulated with a series of 20 pulses during 0.2 ms at a supramaximal intensity. The mean of 20 stimulations is included for statistical analysis.

Compound Muscle Action Potential and Distal Latency. CPAM was measured in gastrocnemius muscle after stimulation of the sciatic nerve. Sciatic nerve was stimulated with a single 0.2 ms pulse at a supramaximal intensity (12.8 mA). The amplitude (mV) and the latency of the response (ms) are measured. The amplitude is indicative of the number of active motor units, while distal latency reflects motor nerve conduction velocity.

Drug Administration. The test compound was administered daily by the i.p. route from the first day of intoxication with the vincristine to the end of the experiments.

Morphometric Analysis. The morphometric analysis was performed on 3 animals per group on sciatic nerve. It includes the measurements of various parameters according to the following procedure:

(1) Dissection of a segment of sciatic nerve (2 cm from the spinal cord, L5-L6, to the trifurcation of the sciatic). The tissue was fixed overnight with glutaraldehyde 4% in phosphate buffer (PH 7.4) and then maintained in 30% sucrose in phosphate buffer at +40° C. until use. The sciatic nerve was fixed in 2% osmium tetroxide in phosphate buffer for 2 hours, dehydrated in serial alcohol solutions and embedded in Eppon. Embedded tissues were then placed at +70° C. for 3 days.

(2) Microtome sections: Transverse sections of 1.5 $\mu$m were made with a microtome and strained with toluidine blue, then dehydrated and mounted in Eurokitt.

(3) Morphometric analysis: Sections were observed using an optical microscope (Nikon) and morphometric analysis were performed with a semi-automated digital image analysis software (Morphonerf, Alcatel). Per slice, 4 fields were analyzed, the number of myelinated fibers, density of fibers, diameter of fibers, thickness of myelin sheath, surface of myelin sheath and G factor.

Results

In Vitro Results. AIT-082 at a concentration of 1 $\mu$M significantly increased survival compared to cisplatin alone (FIG. 1). These effects diminished progressively with higher doses. Neotrofin was 10 times more potent than riluzole and had a greater effect than 5 ng/ml of NGF. AIT-034 was ineffective at all concentrations (0.01–100 $\mu$M).

Figure 2:
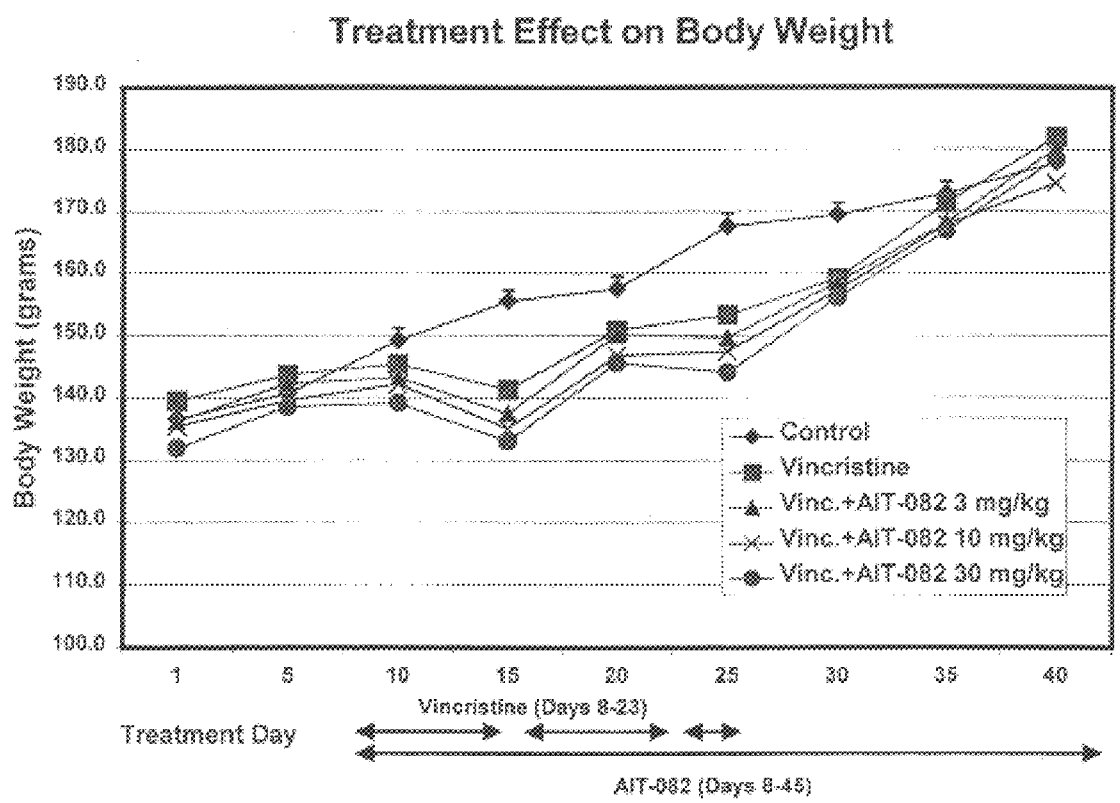
FIG. 2 is a graph showing the effects of vincristine or vincristine plus AIT-082 on body weight.
Figure 3:
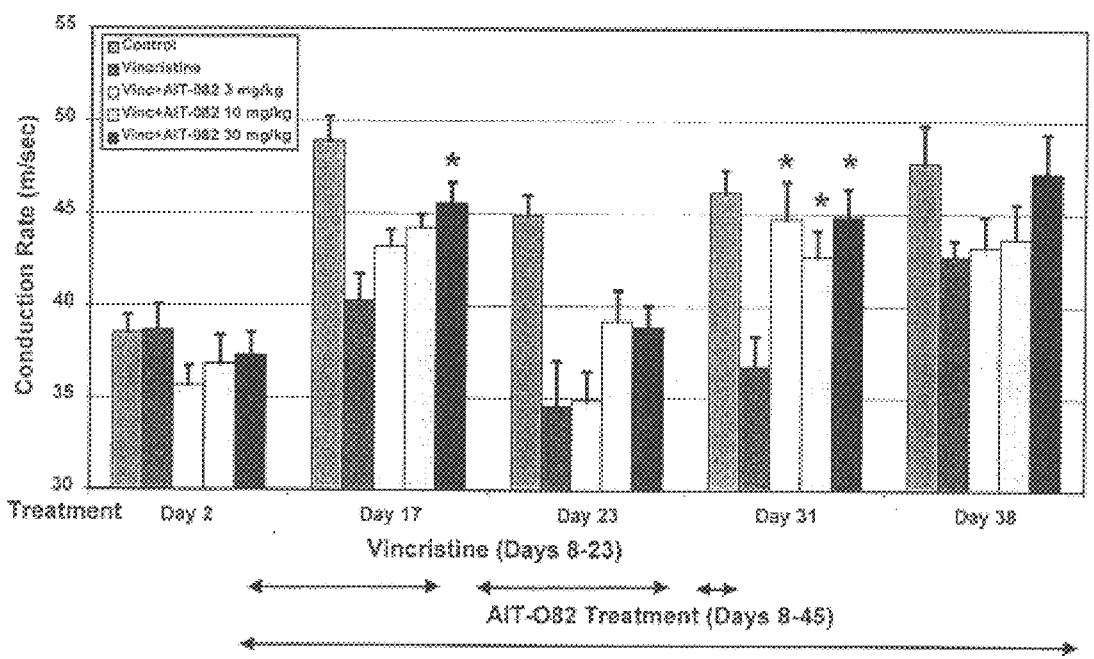
FIG. 3 is a bar graph showing sensory nerve conduction velocity demonstrating the effects of AIT-082 on vincristine-induced neuropathy.
Figure 4:
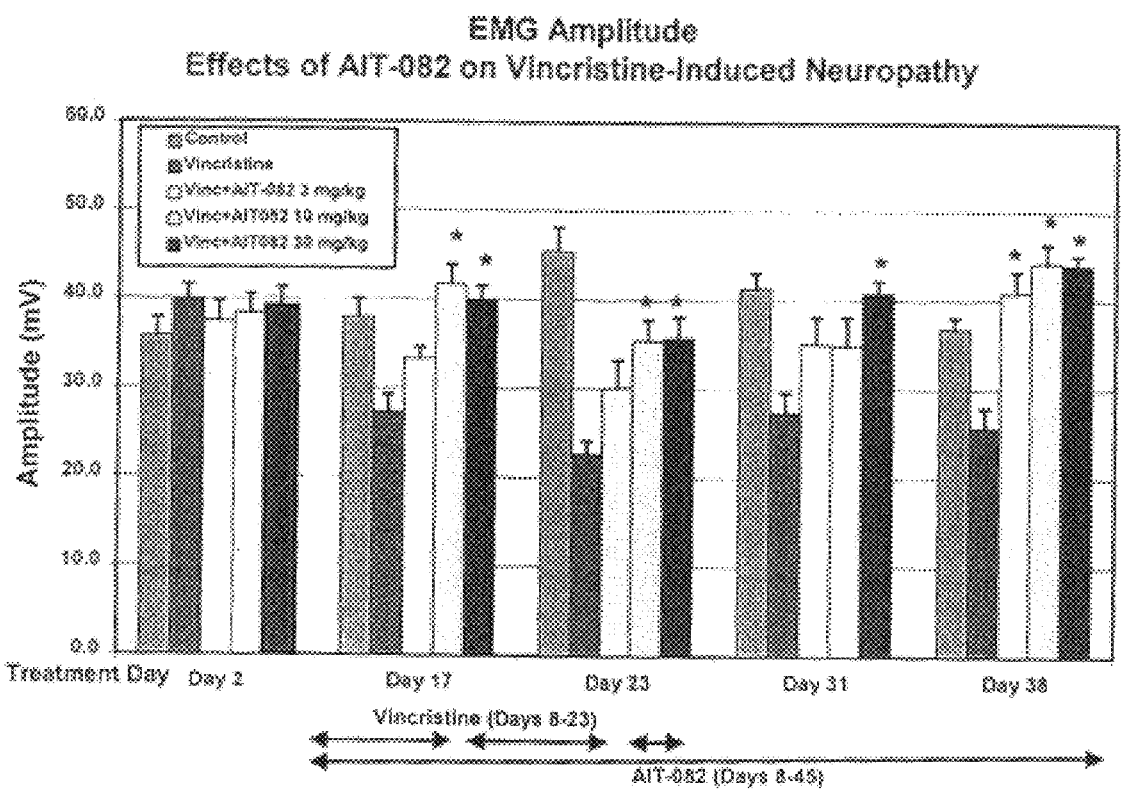
FIG. 4 is a bar graph showing EMG amplitude demonstrating the effects of AIT-082 on vincristine-induced neuropathy.
Figure 5:
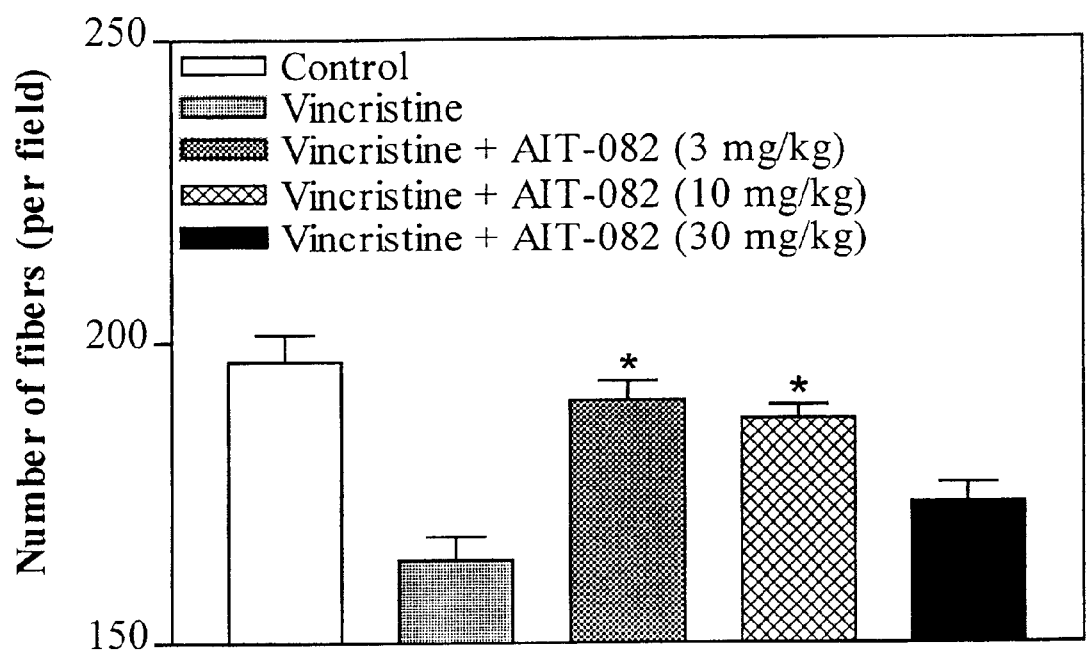
FIG. 5 is a bar graph showing the effect of AIT-082 on the total number of myelinated nerve fibers after vincristine administration.

In Vivo Results. Vincristine treatments (alone and with AIT-082) produced significant reductions in body weight with repetitive dosing compared to day matched controls with vehicle treatment (FIG. 2) at days 11–19 and 22–31. These effects all these treatments were reversible by the termination of treatments. This suggests that the dosage of vincristine and the route of administration did not induce permanent deterioration of health. AIT-082 in combination with vincristine produced a pattern of dose-related reductions in body weight below that observed with control or vincristine alone. The body weights of the animals treated with AIT-082 at 30 mg/kg were significantly lower than treatment with vincristine alone at days 11, 14, 16, 18, 24 and 25. These effects were also reversible and did not appear to effect the improvements in sensory nerve conduction or EMG amplitude described below.

AIT-082 produced significant and dose-related changes in sensory nerve conduction velocity at day 17 during the initial phase of intoxication to vincristine and day 31 during the recovery phase of the study. These finding are suggestive that AIT-082 can lessen the severity of the neuropathy and increase the recovery to normal condition.

AIT-082 produced significant and dose-related changes in EMG amplitude at days 17 and 23 during the initial phase of intoxication to vincristine and days 31 and 38 during the recovery phase of the study. These finding are suggestive that AIT-082 can lessen the severity of the neuropathy and improve recovery. Although these data can not distinguish between effects on muscle responses and effects on nerve conduction, they are supportive of the findings on sensory nerve conduction velocity.

At the end of the treatment periods, AIT-082 treatment was found to have produced greater numbers of myelinated nerve fibers in sciatic nerve biopsies than in animals treated with vincristine alone. These findings are also supportive of either a preventative or regenerative effect of AIT-082 on neurotoxicity induced by vincristine.

Discussion

In an in vitro model for neurotoxicity induced by oncolytic drugs, AIT-082 produced statistically significant protection against cisplatin induced neurotoxicity. These findings indicate that AIT-082 given simultaneously to with an oncolytic drug in patients undergoing cancer therapy could prevent the neuropathic side-effects. Further confirmation of this was obtained from an in vivo model for neurotoxicity induced by oncolytic drugs. In this model, AIT-082 treatment reduced the severity the vincristine induced changes in sensory nerve conduction velocity and electromyographic responses and improved the rate of recovery after the termination of vincristine therapy. The in vivo studies are supportive of a potential use of AIT-082 and related compounds for the prevention of drug-induced neuropathies and also suggest that these compounds could be used to improve recovery from these neuropathies.

Clinical Implications of the Present Findings.

There is increasing evidence that deficient neurotrophic support, including that provided to cutaneous nerves by NGF, contributes to the pathogenesis of drug-induced neuropathies, such as oncolytic therapies. In animal studies, Hayakawa et al. 1998 demonstrated that NGF could prevent neurotoxicity induced by vincristine, taxol and cisplatin. In clinical studies, patients suffering from neurological deficits related to treatments with antitumor agents have low circulating levels of NGF (De Santis et al., 2000).

REFERENCES

K. Hayakawa, T. Itoh, H. Niwa, T. Mutoh and G. Sobue, "NGF prevention of neurotoxicity induced by cisplatin, vincristine and taxol depends on toxicity of each drug and NGF treatment schedule: In vitro study of adult rat sympathetic ganglion explants. Brain Research 794:313–319 (1998)

S. De Santis, A Pace, L. Bove, F. Cognetti, F. Properzi, M. Fiore, V. Triaca, A. Savarese, M. D. Simone, B. Jandolo, L, Manzione and I Aloe. "Patients treated with antitumor drugs displaying neurological deficits are characterized by a low circulating level of Nerve Growth Factor." Clinical Cancer Research 6: 90–95, 2000.

Further, indirect support for this therapeutic approach comes from our earlier findings (Diamond et al., 1988; 1992a) that chronic NGF-deprivation causes a shrinkage of nociceptive fields in the skin consistent with a "dying-back" neuropathy. AIT-082 administration, were it to induce endogenous NGF increases in the skin of patients taking oncolytic drugs, could help protect NGF-sensitive neurons from the threat of neuropathy, without the hazard of hyperalgesia, as explained above.

REFERENCES

The following references are cited in Example 1:

Albers K M, Wright D E, Davis B M (1994) Overexpression of nerve growth factor in epidermis of transgenic mice causes hypertrophy of the peripheral nervous system. *J Neurosci* 14:1422–1432.

Campenot R B (1994) NGF and the local control of nerve terminal growth. *J Neurobiol* 25:599–611

Dantes M and McComas A (1981) The extent and time course of motoneuron involvement in amyotrophic lateral sclerosis. *Muscle and Nerve* 14:416–421.

Davis B M, Fundin B T, Albers K M, Goodness T P, Cronk K M. Rice F L (1997) Overexpression of nerve growth factor in skin causes preferential increases among innervation to specific sensory targets. *J Comp Neurol* 387.489–506

Diamond J, Cooper G and Turner C (1976) Trophic regulation of nerve sprouting. *Science* 193:371–377.

Diamond J, Holmes M and Visheau B (1988) NGF-regulated plasticity in the adult nervous system. *Soc Neurosci Abstr* 14:245.6

Diamond J, Coughlin M, Macintyre L, Holmes M and Visheau B (1987) Evidence that endogenous nerve growth factor is responsible for the collateral sprouting, but not regeneration, of nociceptive axons in adult rats. *Proc Natl Acad Sci USA* 84:6596–6600.

Diamond J, Coughlin M and Holmes M (1992a) Endogenous NGF and impulses regulate the collateral sprouting of sensory nerves in the skin of the adult rat. *J. Neurosci* 12:1454–1466.

Diamond J, Holmes M, Foerster A and Coughlin M (1992b) Sensory nerves in adult rats regenerate and restore sensory function to the skin independently of endogenous NGF. *J. Neurosci* 12:1467–1476.

Doucette R, Diamond J (1987) The normal and precocious sprouting of heat nociceptors in the skin of adult rats. *J. Comp. Neurol* 261:592–603.

English K B, Harpers S, Stayner N, Wang Z M, Davies A M (1994) Localization of nerve growth factor (NGF) and low-affinity NGF receptors in touch domes and quantification of NGF mRNA in keratinocytes of adult rats. *J. Comp. Neurol* 344:470–480.

Gloster A, Diamond J (1992) Sympathetic nerves in adult rats regenerate normally and restore pilomotor function during an anti-NGF treatment that prevents their collateral sprouting. *J. Comp. Neurol* 326:363–374.

Imayarna S (1981) Scanning and transmission electron microscope study on the terminal blood vessels of the rat skin. *J. Invest Dermatol* 76:151–157.

Jackson P C, Diamond J (1984) Temporal and spatial constraints on the collateral sprouting of low-threshold mechanosensory nerves in the skin of rats. *J. Comp. Neurol* 226:336–345.

Karchewski L A, Kim F A, Johnston J, McKnight R M, Verge V M (1999) Anatomical evidence supporting the potential for modulation by multiple neurotrophins in the majority of adult lumbar sensory neurons. *J Comp Neurol* 413(2):327–41.

Korsching S, Theonen H (1985) Nerve growth factor supply for sensory neurons: site of origin and competition with the sympathetic nervous system. *Neurosci Lett* 54:201–205.

Levi-Montalcini R, Skaper S D, Dal Toso R, Petrelli L, Leon A. 1996 Nerve growth factor: from neurotrophin to neurokine. *TINS* 19:514–520.

Lewin G R. Ritter A M, Mendell L M (1993) Nerve growth factor-induced hyperalgesia in the neonatal and adult rat. *J. Neurosci* 13:2136–2148.

Lewin G R, Rueff A, Mendell L M (1994) Peripheral and central mechanisms of NGF-induced hyperalgesia. *Eur J Neurosci* 6:1903–1912.

Mearow K M, Kril Y, and Diamond J (1993) Increased NGF mRNA expression in denervated rat skin. *Neuroreport* 4:351–354.

Murphy R A, Acheson A, Hodges R, Haskins J, Richards C, Reklow E V, Chlumecky V, Barker P A, Alderson R F, Lindsay R M (1993) Immunological relationships of NGF, BDNF and NT3; recognition and functional inhibition by antibodies to NGF. *J. Neurosci* 13:2853–2862.

Neumann S, Doubell T P, Leslie T, Woolf C J. 1996 Inflammatory pain hypersensitivity mediated by phenotypic switch in myelinated primary sensory neurons. *Nature* 384:360–364.

Nixon B J, Doucette R, Jackson P and Diamond J (1984) Impulse activity evokes precocious sprouting of nociceptive nerves into denervated skin. *Somatosensory Res* 2:97–126.

Pertens E, Urschel-Gybers B A, Holmes M, Pal R, Foerster A, Kril Y and Diamond J (1999) Intraspinal and behavioural consequences of NGF-induced nociceptive sprouting and NGF induced hyperalgesia compared in adult rats. *J Comp Neurol* 410:73–89.

Ramer M S, Kawaja M D, Henderson J T, Roder J C, Bisby M A (1998) Glial overexpression of NGF enhances neuropathic pain and adrenergic sprouting into DRG following sciatic nerve constriction in mice. *Neurosci Lett* 251 53–56

Romero M I, Rangappa N, Li L, Lightfoot E, Garry M G, Smith G M (2000) Extensive sprouting of sensory afferents and hyperalgesia induced by conditional expression of nerve growth factor in the adult spinal cord. *J Neurosci* 20:4435–4445

Stucky C L, Koltzenburg M, Schneider M, Engle M G, Albers K M, Davis B M (1999) Overexpression of nerve growth factor in skin selectively affects the survival and functional properties of nociceptors. *J Neurosci* 19:8509–8516

Theriault E, Diamond J (1988) Nociceptive cutaneous stimuli evoke localized contractions in a skeletal muscle. *J Neurophysiol* 60:446–462.

Toma J G, Rogers D, Senger D I, Campenot R B, Miller F D (1997) Spatial regulation of neuronal gene expression in response to nerve growth factor. *Dev Biol* 184: 1–9

Yasargil G M, Macintyre L, Doucette R, Visheau B, Holmes M and Diamond J (1988) Axonal domains within

EXAMPLE 2

Further Neuroprotective Effects of AIT-082

The objectives of the studies described in this application are to evaluate AIT-082 and related analogues for their potential utility in the treatment of neuropathies associated with oncolytic therapies. The prototypic compound, AIT-082, is currently in Phase 2 clinical trials for Alzheimer's disease (AD) and has been proven safe in over 1400 patients. Its preclinical pharmacological effects include neuroprotection against excitotoxicity, induction of the synthesis and secretion of neurotrophic and pleiotropic factors, neuroregenerative effects and proliferative effects on neural progenitor cells. The effects of AIT-082 are unlike any product that has been approved or is currently under evaluation for neuropathies associated with oncolytic agents. AIT-082 and its second generation analogues may arrest or retard neurodegenerative processes, promote neuroregeneration and provide symptomatic relief for cancer patients with neuropathies or at high risk of developing neuropathies.

Background: AIT-082 (Neotrofin™, leteprinim potassium, 4[[3(1,6-dihydro-6-oxo-9-purin-9-yl)-1-oxopropyl]amino]benzoic acid, potassium salt) is a novel therapeutic agent currently in clinical testing for the treatment of AD. The proposed preclinical studies and clinical trials for AIT-082 in oncolytic therapy-induced neuropathies are based upon its neuroprotective, neurotrophic and neuroregenerative effects in preclinical research. These effects may prevent or reverse the progressive degenerative changes associated with oncolytic therapies.

In vitro Effects on Expression and Secretion of Nerve Growth Factors: Modulation of the secretion or efficacy of neurotrophic factors may have a major role in preventing or reversing neuropathies due to oncolytic therapies[3,4]. Findings from studies with rat astrocyte cultures provided evidence that AIT-082 increases the production of mRNAs for several neurotrophic factors, including NGF, basic fibroblast growth factor (bFGF), and neurotrophin 3 (NT-3)[1,2]. In astrocytes, AIT-082 enhanced the secretion into the culture medium of the neurotrophic proteins NGF, TGF and S 100[5]. The secretion of NGF and TGF were dependent upon de novo protein synthesis induced by AIT-082 as indicated by the suppression of these effects by cycloheximide pre-treatment The secretion of S 100 was independent of protein synthesis and from existing cellular stores after AIT-082 treatment.

In vivo Effects on Expression and Secretion of Nerve Growth Factors: In attempt to further explore the effects of AIT-082 that could be beneficial for chemotherapy-induced neuropathy, additional studies were conducted on dose-related effects on BDNF levels in the spinal cord. In these studies, AIT-082 was administered in drinking water for 7 days and BDNF content was measured by ELISA assay. AIT-082 produced significant dose-related increases in BDNF levels in the rat spinal cord.

The following are the references for Example 2:

1. Glasky A J, Glasky M S, Ritzmann R F and Rathbone M P. AIT-082, a novel purine derivative with neuroregenerative properties. Exp. Opin. Invest. Drugs. 6:1413–1417, 1997.

2. Rathbone M P, Middlemiss P J, Gysbers J, Diamond J, Holmes M, Pertens E, Juurlink B H, Glasky A, Ritzmann R, Glasky M, Crocker C E, Ramirez J J, Lorenzen A, Fein T, Schultze E, Schwabe U, Cicarelli R, Di Iorio P, and Caciagli F. Physiology and pharmacology of natural and synthetic nonadenine-based purines in the nervous system. Drug. Devel. Res. 45:356–372,1998.

3. Hayakawa K, Sobue G, Itoh T. Nerve growth factor prevents neurotoxic effects of cisplatin, vincristine and taxol, on adult rat sympathetic gang lion explants in vitro. Life Sci 55:591–525, 1994.

4. Hayakawa K, Itoh T, Niwa H, Mutoh T, Sobue G, NGF prevention of neurotoxicity induced by cisplatin, vincristine and taxol depends on toxicity of each drug and NGF treatment schedule: in vitro study of adult rat sympathetic gang lion explants. Brain Res 794:313–319,1998.

5. Middlemiss P. Glasky A J, Rathbone M P, Werstuik E, Hindley S and Gysbers J. AIT-082, a unique purine derivative, enhances nerve growth factor mediated outgrowth from PC12 cells. Neurosci. Letters 199:1–4, 1995.

Advantages of the Invention

The present invention provides new methods for treating patients with drug-induced peripheral neuropathy, including peripheral neuropathy associated with the administration of oncolytic drugs, to induce peripheral nerve sprouting, which can include nociceptive nerve sprouting. These methods provide for nerve regeneration. These methods can be performed, at least in some alternatives, without inducing hyperalgesia. These methods can be combined with other treatments for drug-induced peripheral neuropathy, such as palliative measures for the relief of pain. They do not depend on specific interactions between the compounds administered and the drugs causing peripheral neuropathy.

Although the present invention has been described inconsiderable detail, with reference to certain preferred versions thereof, other versions and embodiments are possible. Therefore, the scope of the invention is determined by the following claims.

We claim:

1. A method of treating drug-induced neuropathy comprising administering to a patient with drug-induced neuropathy in effective amount of N-4-carboxyphenyl-3-(6-oxohydropurin-9-yl) propanamide, also known as AIT-082, wherein said neuropathy is induced by an oncolytic drug selected from the group consisting of a vinca alkaloid, cisplatin, paclitaxel, suramin, altretamine, carboplatin, chlorambucil, cytarabine, dacarbazine, docetaxel, etoposide, fludarabine, ifosfamide with mesna, tamoxifen, teniposide, and thioguanine.

2. The method of claim 1 wherein the action of the compound having activity against drug-induced neuropathy is to induce upregulation of neurotrophic factor synthesis.

3. The method of claim 2 wherein the neurotrophic factor is selected from the group consisting of NGF, NT-3, BDNF, and NT-4/5.

4. The method of claim 1 wherein the administration of the compound having activity against drug-induced neuropathy induces peripheral nerve sprouting in the skin of the patient to whom the compound was administered.

5. The method of claim 4 wherein the peripheral nerve sprouting is nociceptive nerve sprouting.

6. The method of claim 5 wherein the nociceptive nerve sprouting is induced without the occurrence of hyperalgesia.

7. The method of claim 1 wherein the oncolytic drug is vincristine.

8. The method of claim 1 wherein the oncolytic drug is paclitaxel.

9. The method of claim 1 wherein the oncolytic drug is cisplatin.

* * * * *